United States Patent
Castelli

(12) 
(10) Patent No.: US 12,035,920 B2
(45) Date of Patent: Jul. 16, 2024

(54) ULNAR COMPRESSION DEVICE

(71) Applicant: Medtronic Vascular, Inc., Santa Rosa, CA (US)

(72) Inventor: Brian Castelli, Rohnert Park, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/819,765

(22) Filed: Aug. 15, 2022

(65) Prior Publication Data

US 2022/0387047 A1    Dec. 8, 2022

Related U.S. Application Data

(62) Division of application No. 16/529,383, filed on Aug. 1, 2019, now Pat. No. 11,446,040.

(Continued)

(51) Int. Cl.
*A61B 17/135*    (2006.01)
*A61B 17/00*    (2006.01)
*A61M 5/42*    (2006.01)

(52) U.S. Cl.
CPC .......... *A61B 17/135* (2013.01); *A61M 5/425* (2013.01); *A61B 2017/00955* (2013.01)

(58) Field of Classification Search
CPC ........ A61B 2017/12004; A61B 17/132; A61B 17/135; A61B 17/1322; A61B 17/1325; A61B 17/1327; A61B 17/1355; A61B 2017/00557; A61B 2017/00907; A61B 2017/00955; A61F 5/012; A61F 5/05866; A61F 5/013; A61F 5/01; A61F 5/0118; A61F 5/05816; A61F 5/05875; A61F 5/30; A61F 2007/0001; A61F 2007/0029;

(Continued)

(56) References Cited

U.S. PATENT DOCUMENTS

2004/0193084 A1\* 9/2004 Ravikumar ........... A61F 13/069
  602/13
2015/0335334 A1\* 11/2015 Pancholy ............. A61B 5/0295
  606/202

(Continued)

OTHER PUBLICATIONS

Mechanical Definition Merriam Webster, https://www.merriam-webster.com/dictionary/mechanical, accessed Feb. 13, 2024, copyright Merriam-Webster, Incorporated, 2024 (Year: 2024).\*

(Continued)

*Primary Examiner* — Kankindi Rwego
(74) *Attorney, Agent, or Firm* — Shumaker & Sieffert, P.A.

(57) ABSTRACT

In some examples, a tissue compression device includes a base including a major surface configured to engage a dorsal surface of a hand of a patient, a flexible backing adjustably mechanically connected to the base and configured to engage a palmar surface of the hand when the dorsal surface of the hand is engaged with the base, and an expandable member mechanically connected to the flexible backing. The expandable member is configured to be positioned over an ulnar region of the patient when the palmar surface of the hand is engaged with the flexible backing and the dorsal surface of the hand is engaged with the base, such that inflation of the expandable member may apply pressure to tissue near the ulnar artery of the patient.

9 Claims, 10 Drawing Sheets

Related U.S. Application Data

(60) Provisional application No. 62/736,241, filed on Sep. 25, 2018, provisional application No. 62/714,865, filed on Aug. 6, 2018.

(58) Field of Classification Search
CPC ...... A61F 2007/0036; A61F 2007/0037; A61F 2007/0038; A61M 5/425
USPC ................................. 606/201, 202, 203, 204
See application file for complete search history.

(56) References Cited

U.S. PATENT DOCUMENTS

2016/0174952 A1\* 6/2016 Shah .................. A61B 17/0057
606/213
2019/0167273 A1\* 6/2019 Morrison ............. A61B 17/135

OTHER PUBLICATIONS

Communication pursuant to Article 94(3) EPC from counterpart European Application No. 19880962.6 dated May 23, 2023, 4 pp.

\* cited by examiner

ULNAR COMPRESSION DEVICE

This application is a divisional of U.S. application Ser. No. 16/529,383, filed on Aug. 1, 2019, and entitled, "ULNAR COMPRESSION DEVICE," and which was granted as U.S. Pat. No. 11,446,040 on Sep. 20, 2022, which claims the benefit of U.S. Provisional Application Ser. No. 62/714,865, entitled "DISTAL RADIAL COMPRESSION DEVICE," and filed on Aug. 6, 2018, and claims the benefit of U.S. Provisional Application Ser. No. 62/736,241, entitled "ULNAR COMPRESSION DEVICE," and filed on Sep. 25, 2018, the entire content of each of which are incorporated herein by reference.

TECHNICAL FIELD

This disclosure relates to tissue compression devices.

BACKGROUND

Medical catheters may be advanced through an access site into vasculature of a patient to provide a lumen through which medical devices or therapeutic agents may be introduced to reach a treatment site. For example, the access site for percutaneous coronary procedures may include the radial artery or the femoral artery of a patient.

SUMMARY

The present disclosure describes tissue compression devices and techniques to apply pressure to an ulnar region of a patient before, during, and/or after a transradial access procedure. The ulnar region may include tissue at or near (e.g., superficial to) an ulnar artery and/or ulnar veins in an arm of the patient. Application of pressure at the ulnar region may be used to facilitate transradial access, reduce occlusion of the radial artery after transradial procedure, or both. In some examples, a tissue compression device includes a base including a major surface configured to engage a dorsal surface of a hand of a patient; a flexible backing configured to be adjustably mechanically connected to the base and configured to engage a palmar surface of the hand when the dorsal surface of the hand is engaged with the base; and an expandable member mechanically connected to the flexible backing. The expandable member is configured to be positioned over an ulnar region of the patient when the palmar surface of the hand is engaged with the flexible backing and the dorsal surface of the hand is engaged with the base. The expandable member also is configured to apply pressure to the ulnar region before, during, and/or after a transradial access procedure.

In other examples, a tissue compression device has a band-like configuration (e.g., a bracelet-like configuration) and includes a first expandable member configured to be positioned over (e.g., superficial to) an ulnar region of the patient and a second expandable member configured to be positioned over an radial artery of the patient when the device is positioned on an arm of a patient.

Clause 1: In some examples, a tissue compression device comprises a base comprising a major surface configured to engage a dorsal surface of a hand of a patient; a flexible backing adjustably mechanically connected to the base and configured to engage a palmar surface of the hand when the dorsal surface of the hand is engaged with the base; and an expandable member mechanically connected to the flexible backing, the expandable member configured to be positioned over an ulnar region of the patient when the palmar surface of the hand is engaged with the flexible backing and the dorsal surface of the hand is engaged with the base, and the expandable member configured to apply pressure to the ulnar region.

Clause 2: In some examples, a tissue compression device comprises a rigid base comprising a major surface configured to engage a dorsal surface of a hand of a patient; a radial lip extending from the major surface and configured to engage a radial border of the hand when the dorsal surface of the hand is engaged with the base; and a ulnar lip extending from the major surface and configured to engage an ulnar border of the hand when the dorsal surface of the hand is engaged with the base; an inextensible flexible backing adjustably mechanically connected to the base and configured to engage a palmar surface of the hand to urge the dorsal surface of the hand toward the major surface of the base; and an expandable member mechanically connected to the flexible backing, the expandable member configured to be positioned over an ulnar region of the patient when the palmar surface of the hand is engaged with the flexible backing and the dorsal surface of the hand is engaged with the base, and the expandable member configured to inflate to increase the volume of the expandable member.

Clause 3: In some examples of the tissue compression device of clause 1 or clause 2, the expandable member comprises a bladder configure to inflate to at least a pressure to cause compression of tissue near an ulnar artery of the patient.

Clause 4: In some examples of the tissue compression device of any one of clauses 1 through 3, the base comprises a plurality of base attachment structures, the flexible backing comprises a plurality of backing attachment structures, and each backing attachment structure of the plurality of backing attachment structures is configured to adjustably mechanically connect the flexible backing to a respective base attachment structure of the plurality of base attachment structures.

Clause 5: In some examples of the tissue compression device of clause 4, at least one backing attachment structure of the plurality of backing attachment structures is configured to adjust a tension of the flexible backing to urge the dorsal surface of the hand of the patient toward the major surface of the base when the palmar surface of the hand is engaged with the flexible backing.

Clause 6: In some examples of the tissue compression device of any one of clauses 1 through 5, the expandable member is removably mechanically connected to the flexible backing.

Clause 7: In some examples of the tissue compression device of any one of clauses 1 through 5, the expandable member is integrally formed with the flexible backing.

Clause 8: In some examples of the tissue compression device of any one of clauses 1 through 7, the flexible backing comprises a substantially inextensible material.

Clause 9: In some examples of the tissue compression device of any one of clauses 1 through 8, at least one of the base or the flexible backing is configured to engage a left hand of the patient, a right hand of the patient, or both the left hand and the right hand of the patient.

Clause 10: In some examples of the tissue compression device of any one of clauses 1 through 9, the base comprises a substantially rigid thermoplastic or a substantially rigid thermoset plastic.

Clause 11: In some examples of the tissue compression device of any one of clauses 1 through 9, the base is configured to reduce a range of motion of a digit of the hand or a portion of a wrist of the patient when the dorsal surface of the hand is engaged with the first major surface of the base.

Clause 12: In some examples of the tissue compression device of any one of clauses 1 through 11, the base comprises a first lip extending from the major surface and configured to engage an ulnar border of the hand when the dorsal surface of the hand is engaged with the base; and a second lip extending from the major surface and configured to engage a radial border of the hand when the dorsal surface of the hand is engaged with the base.

Clause 13: In some examples of the tissue compression device of any one of clauses 1 through 12, the base is configured to position the hand of the patient in a predetermined configuration when the dorsal surface of the hand is engaged with the major surface of the base.

Clause 14: In some examples of the tissue compression device of any one of clauses 1 through 13, the expandable member comprises a first expandable member, and the tissue compression device further comprises a second expandable member mechanically connected to the flexible backing, the second expandable member configured to be positioned over a radial region of the patient when the palmar surface of the hand is engaged with the flexible backing and the dorsal surface of the hand is engaged with the base, the second expandable member being configured to apply pressure to the radial region.

Clause 15: In some examples of the tissue compression device of clause 14, the second expandable member comprises a bladder configure to inflate to at least a pressure to cause patent hemostasis of a vascular access site at the radial artery of the patient.

Clause 16: In some examples of the tissue compression device of clause 14 or 15, the second expandable member is configured to be detached and subsequently reattached to the flexible backing.

Clause 17: In some examples, a method includes mechanically connecting a flexible backing of a tissue compression device to a first base attachment structure of a plurality of base attachment structures defined by or extending from a major surface of a base of the tissue compression device, the major surface configured to engage a dorsal surface of a hand of a patient; and mechanically connecting the flexible backing to a second base attachment structure of the plurality of base attachment structures, the flexible backing configured to be adjustably mechanically connected to the base, the tissue compression device further comprising an expandable member mechanically connected to the flexible backing, the expandable member configured to be positioned over an ulnar region of the patient when the dorsal surface of the hand is engaged with the major surface of the base, the expandable member configured to apply pressure to tissue near an ulnar artery of the patient.

Clause 18: In some examples of the method of clause 17, the method further comprises positioning the dorsal surface of the hand of the patient on the major surface of the base.

Clause 19: In some examples of the method of clause 18, positioning the dorsal surface of the hand on the major surface of the base comprises positioning the dorsal surface of the hand on the major surface of the base prior to mechanically connecting the flexible backing to the second base attachment structure.

Clause 20: In some examples of the method of clause 18, positioning the dorsal surface of the hand on the major surface of the base comprises positioning the dorsal surface of the hand on the major surface of the base after mechanically connecting the flexible backing to the second base attachment structure.

Clause 21: In some examples of the method of any one of clauses 18 through 20, the method further comprises, after positioning the dorsal surface of the hand of the patient on the major surface of the base, inflating the expandable member to cause compression of tissue near the ulnar artery.

Clause 22: In some examples of the method of any one of clauses 18 through 21, the method further comprises, after positioning the dorsal surface of the hand of the patient on the major surface of the base, adjusting a position of the expandable member relative to the hand of the patient.

Clause 23: In some examples of the method of clause 22, adjusting the position of the expandable member relative to the hand of the patient comprises loosening or tightening a mechanical connection between the flexible backing and at least one of the first or second base attachment structures.

Clause 24: In some examples of the method of clause 22, adjusting the position of the expandable member relative to the hand of the patient comprises detaching the expandable member from the flexible backing and subsequently reattaching the expandable member to the flexible backing.

Clause 25: In some examples of the method of any one of clauses 17 through 24, the flexible backing comprises a plurality of backing attachment structures, and mechanically connecting the flexible backing to the first base attachment structure comprises adjustably mechanically connecting a first backing attachment structure of the plurality of backing attachment structures to the first base attachment structure, and mechanically connecting the flexible backing to the second base attachment structure comprises adjustably mechanically connecting a second backing attachment structure of the plurality of backing attachment structures to the second base attachment structure.

Clause 26: In some examples of the method of any one of clauses 17 through 25, at least one base attachment structure of the plurality of base attachment structures is integrally formed with the major surface.

Clause 27: In some examples of the method of any one of clauses 17 through 25, at least one base attachment structure of the plurality of base attachment structures is physically separate from the major surface, and the method further comprises, before mechanically connecting the flexible backing to the first base attachment structure, attaching the at least one base attachment structure of the plurality of base attachment structures to the major surface.

Clause 28: In some examples of the method of any one of clauses 17 through 27, the base comprises a first lip extending from the major surface and configured to engage an ulnar border of the hand when the dorsal surface of the hand is engaged with the base; and a second lip extending from the major surface and configured to engage a radial border of the hand when the dorsal surface of the hand is engaged with the base.

Clause 29: In some examples of the method of any one of clauses 17 through 28, the expandable member is integrally formed with the flexible backing.

Clause 30: In some examples of the method of any one of clauses 17 through 29, the flexible backing comprises a substantially inextensible material.

Clause 31: In some examples of the method of any one of clauses 17 through 30, the base is configured to reduce a range of motion of a digit of the hand or a portion of a wrist of the patient when the dorsal surface of the hand is engaged with the major surface of the base.

Clause 32: In some examples of the method of any one of clauses 17 through 31, the base is configured to position the hand of the patient in a predetermined configuration when the dorsal surface of the hand is engaged with the major surface of the base.

Clause 33: In some examples of the method of any one of clauses 17 through 32, the method further comprises forming the base from a substantially rigid thermoplastic or a substantially rigid thermoset plastic.

Clause 34: In some examples of the method of any one of clauses 17 through 33, the method further comprises cutting the flexible backing from a substantially inextensible material.

Clause 35: In some examples of the method of any one of clauses 17 through 34, the method further comprises attaching the expandable member to the flexible backing by at least one of adhering, welding, or mechanically fastening the expandable member to the flexible backing.

Clause 36: In some examples of the method of any one of clauses 17 through 35, the expandable member comprises a first expandable member and the tissue compression device further comprises a second expandable member mechanically connected to the flexible backing, and the method further comprises, after positioning the dorsal surface of the hand of the patient on the major surface of the base, adjusting a position of the second expandable member to position the second expandable member over a radial artery of the patient.

Clause 37: In some examples of the method of clause 36, the method further comprises, after adjusting a position of the second expandable member, inflating the second expandable member to apply pressure to a radial artery of the patient to cause patent hemostasis of a vascular access site at the radial artery.

Clause 38: In some examples of the method of any one of clauses 17 through 35, the tissue compression device further comprises a second expandable member mechanically connected to the flexible backing, and the method further comprises, after positioning the dorsal surface of the hand of the patient on the major surface of the base, inflating the second expandable member to apply pressure to a radial artery of the patient to cause patent hemostasis of a vascular access site at the radial artery.

Clause 39: In some examples, a tissue compression device comprises a band configured to engage a wrist of a patient; a first expandable member mechanically connected to the band, the first expandable member being configured to be positioned over an ulnar region of the patient when the band is engaged with the wrist of the patient, the first expandable member being configured to apply pressure to the ulnar region; and a second expandable member mechanically connected to the band, the second expandable member being configured to be positioned over a radial region of the patient when the band is engaged with the wrist of the patient, and the second expandable member being configured to apply pressure to the radial region.

Clause 40: In some examples of the tissue compression device of clause 39, the band comprises a base comprising a major surface configured to engage a first portion of the wrist of the patient; and a flexible backing adjustably mechanically connected to the base and configured to engage a second portion of the wrist of the patient, the first expandable member is mechanically connected to at least one of the base or the flexible backing, and the second expandable member is mechanically connected to at least one of the base or the flexible backing.

Clause 41: In some examples of the tissue compression device of clause 39 or 40, the first expandable member comprises a first bladder configured to inflate to at least a pressure to cause compression of tissue near an ulnar artery of the patient, and the second expandable member comprises a second bladder configure to inflate to at least a pressure to cause patent hemostasis of a vascular access site at the radial artery of the patient.

Clause 42: In some examples of the tissue compression device of any one of clauses 40 through 41, the base comprises at least one base attachment structure, the flexible backing comprises at least one backing attachment structure, and the at least one backing attachment structure is configured to adjustably mechanically connect the flexible backing to the at least one base attachment structure.

Clause 43: In some examples of the tissue compression device of clause 42, the at least one backing attachment structure is configured to adjust a tension of the flexible backing to urge at least one of the first expandable member or the second expandable member toward the wrist of the patient when the wrist of the patient is engaged with the band.

Clause 44: In some examples of the tissue compression device of any one of clauses 39 through 43, at least one of the first expandable member or the second expandable member is removably mechanically connected to the band.

Clause 45: In some examples of the tissue compression device of any one of clauses 39 through 43, at least one of the first expandable member or the second expandable member is integrally formed with the band.

Clause 46: In some examples of the tissue compression device of any one of clauses 40 through 45, the flexible backing comprises a substantially inextensible material.

Clause 47: In some examples of the tissue compression device of any one of clauses 39 through 46, the band is configured to engage a left wrist of the patient, a right wrist of the patient, or both the left wrist and the right wrist of the patient.

Clause 48: In some examples of the tissue compression device of any one of clauses 40 through 47, the base comprises a substantially rigid thermoplastic or a substantially rigid thermoset plastic.

Clause 49: In some examples of the tissue compression device of any one of clauses 40 through 48, the base is shaped to correspond to an anatomical shape of at least part of the wrist of the patient.

Clause 50: In some examples of the tissue compression device of any one of clauses 40 through 49, the base and the flexible backing are integrally formed.

Clause 51: In some examples, a method includes using the tissue compression device of any one of clauses 39 through 50.

Clause 52: In some examples, a method includes forming the tissue compression device of any one of clauses 39 through 50.

The details of one or more examples are set forth in the accompanying drawings and the description below. Other features, objects, and advantages will be apparent from the description and drawings, and from the claims.

DETAILED DESCRIPTION

Figure 1A:
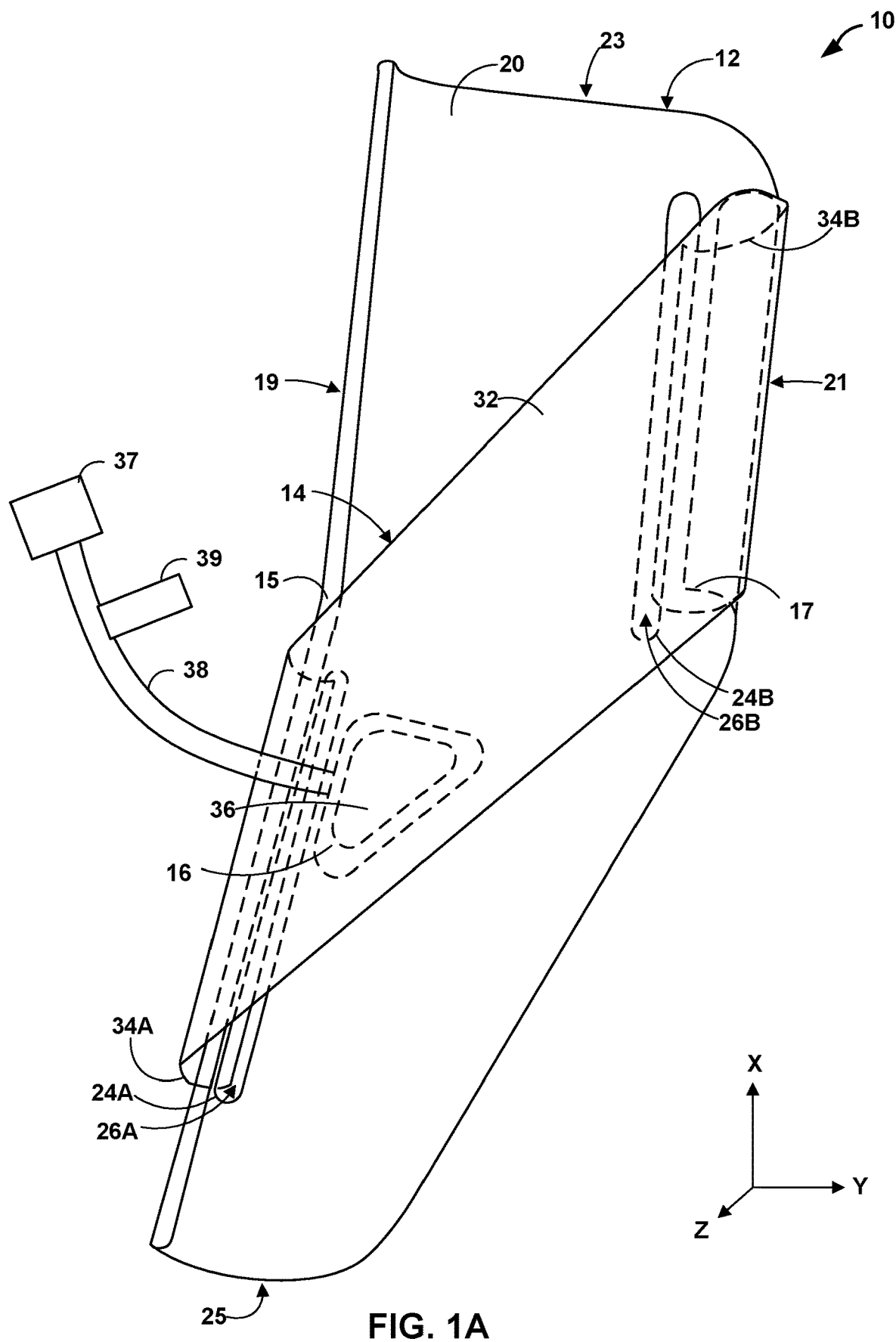
FIG. 1A is a conceptual perspective view of an example tissue compression device including a flexible backing adjustably mechanically connected to a base and an expandable member mechanically connected to the flexible backing.

Percutaneous coronary procedures with transradial access may result in radial artery occlusion (e.g., acute and/or chronic radial artery occlusion). Radial artery occlusion may be caused by acute thrombosis due to intimal abrasion and vessel injury in conjunction with blood flow cessation when pressure is applied to the radial artery access site (e.g., radial compression) to achieve hemostasis. Radial artery occlusion may be undesirable. For example, radial artery occlusion may limit future ipsilateral transradial access, cause transient discomfort to the patient, or any combination thereof.

The disclosure describes tissue compression devices configured to apply pressure to an ulnar region of a patient, as well as techniques for forming and using the tissue compression devices. Example tissue compression devices described herein are configured to apply pressure to tissue at the ulnar region to compress the ulnar artery, the ulnar vein, or both and may include a base, a flexible backing adjustably mechanically connected to the base, and an expandable member mechanically connected to the flexible backing. The ulnar region may include selected tissue near (e.g., superficial to) an ulnar artery and/or an ulnar vein of the patient. In some examples, the base and the flexible backing are configured to engage the hand of the patient (e.g., at least one of the hand, the wrist, and the forearm of the patient) to position the expandable member over the ulnar region proximal the hand of the patient. By engaging the hand of the patient, the tissue compression device may reduce movement of the expandable member relative to the ulnar region, which may enable the tissue compression device to more consistently apply pressure to the ulnar region.

The tissue compression device is configured to apply pressure to selected tissue beneath the expandable member, e.g., to tissue that transmits the pressure to the ulnar artery or ulnar vein. It is believed that ipsilateral ulnar artery compression (also referred to as ulnar compression) may maintain or increase radial artery blood flow during radial compression to reduce incidence of radial artery occlusion compared to other methods alone, such as compared to the use of a low sheath (part of the percutaneous access device) to artery size ratio, the use of intraprocedural heparin, or the maintenance of radial artery patency during hemostasis after transradial access. Ulnar compression may result in complete or near complete occlusion of the ulnar artery to increase blood flow in the radial artery. The increased blood flow in the radial artery may enable compression of the radial artery with a pressure sufficient to achieve hemostasis at the transradial access site without causing radial artery occlusion. In this way, the disclosed tissue compression device may reduce incidence of radial artery occlusion and improve the healing process after percutaneous coronary procedures with transradial access compared to other methods.

Additionally, it is believed that ulnar artery compression may improve the outcomes or ease of transradial percutaneous coronary procedures by facilitating access to the vasculature of the patient. For example, a weak radial pulse due to a relatively small radial artery, a relatively deep radial artery, or hypotension may make vasculature access by arteriotomy of the radial artery difficult. It is believed that ulnar compression may be used to improve accuracy and speed of vasculature access via arteriotomy of the radial artery by making radial pulse stronger and/or enlarging the radial artery to improve success rate of fingertip palpitation-guided access to the radial artery.

FIG. 1A is a conceptual perspective view illustrating an example tissue compression device 10 including a base 12, a flexible backing 14 adjustably mechanically connected to base 12, and an expandable member 16 mechanically connected to flexible backing 14. Tissue compression device 10 may be configured to receive and engage a hand of a patient to apply pressure to selected tissue at the ulnar region (e.g., aligned with but superficial to the ulnar artery and/or ulnar vein) of the patient to thereby apply pressure to the ulnar artery and/or ulnar vein. The selected tissue may be proximal the wrist of the patient, such as immediately proximal the wrist or a greater distance proximal to the wrist (e.g., between about 1 centimeter and about 15 centimeters proximal to the wrist), distal the wrist, such as on a portion of the hand of the patient, or on the wrist.

Figure 1B:
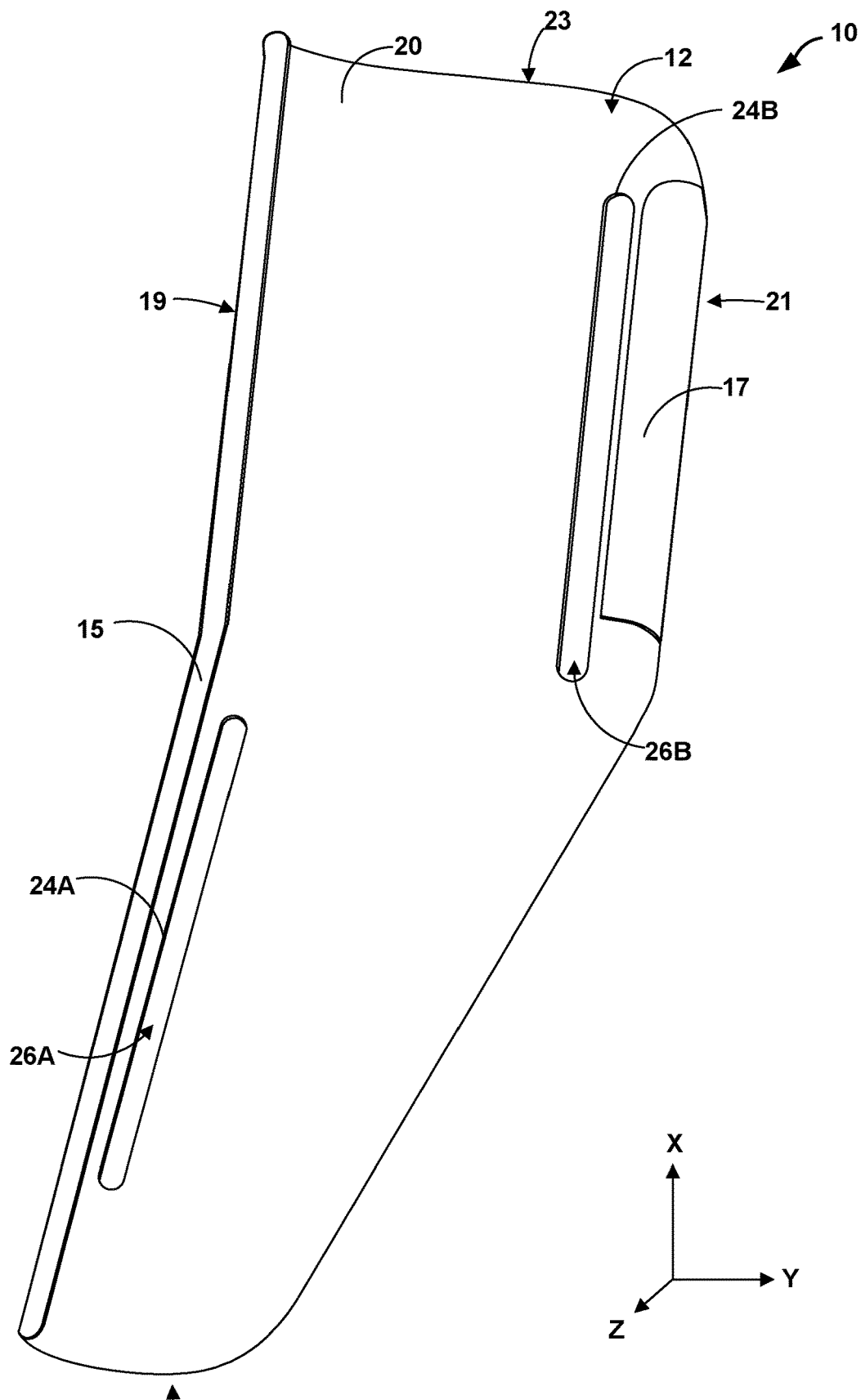
FIG. 1B is a conceptual perspective view of the base of the example tissue compression device illustrated in FIG. 1A.

FIG. 1B is a conceptual perspective view of base 12 of tissue compression device 10 illustrated in FIG. 1A. FIG. 1B illustrates tissue compression device 10 without flexible backing 14. Base 12 defines a first major surface 20 and a second major surface 22 (not visible in FIGS. 1A and 1B, shown in FIG. 3) on an opposite side of base 12 from first major surface 20. First major surface 20 and second major surface 22 face in different directions. First major surface 20 may include any suitable shape configured to engage with at least a portion of the hand, wrist, and/or forearm of the patient. For example, as illustrated in FIGS. 1A and 1B, first major surface 20 may have a shape in the X-Y plane (orthogonal X-Y-Z axes are shown in the figures for ease of description only) that corresponds to an anatomical shape of at least part of a right hand or a left hand of a patient (e.g., mimics the general outline of the footprint of a hand or part of the footprint of the hand). In some examples, first major surface 20 may have a shape in the X-Y plane that corresponds to an anatomical shape of both the right hand and the left hand of the patient, e.g., first major surface 20 may be ambidextrous. In other examples, first major surface 20 may have other shapes, such as elliptical, rectangular, or irregular shapes.

In some examples, second major surface 22 may be shaped the same as or substantially similar to first major surface 20, which may permit second major surface 22 to be used to engage the other hand of a patient if first major surface 20 is configured to engage with only the left hand or the right hand. For example, second major surface 22 may be a mirror image of the shape of first major surface 20 such that second major surface 22 has a shape that corresponds to an anatomical shape of either the right hand or the left hand of the patient and first major surface 20 has a shape that corresponds to an anatomical shape of the other of the left hand or the right hand of the patient. In this way, base 12 may be shaped to engage both the left hand of the patient and the right hand of the patient by inverting base 12 to engage the dorsal surface of the hand of the patient with one of the first major surface 20 or second major surface 22.

In some examples, base 12 has a three-dimensional shape configured to position the hand of the patient in a predetermined configuration or reduce a range of motion of a digit of the hand or a portion of the wrist of the patient when a surface of the hand is positioned over first major surface 20 of base 12. The predetermined configuration may include, for example, a flat (e.g., the hand may sit flat on a planar surface) or a non-flat hand configuration, a partially bent position of one or more digits (e.g., fingers or the thumb) or the wrist of the patient (e.g., a flexed position or a cupped or grasped position), an extended position of one or more digits or the wrist of the patient, or a combination thereof. For example, base 12 may be shaped such that first major surface 20 is shaped to correspond to a shape of a dorsal surface of the hand of the patient in the predetermined configuration, such that base 12 includes one or more structures configured to correspond to the position of one or more digits or the wrist of the patient in the predetermined configuration, or both.

In some examples, base 12 defines a lip 15 and/or 17, which are each example structures configured to help hold the hand of the patient in a particular configuration or reduce a range of motion of a digit of the hand or a portion of the wrist of the patient when the dorsal surface of the hand is engaged with first major surface 20 of base 12. For example, first lip 15 (e.g., ulnar lip) may be configured to engage at least a portion of the ulnar border of the hand of the patient when the dorsal surface of the hand is engaged with first major surface 20. In some examples, first lip 15 extends from an ulnar side 19 of base 12 to at least partially surround the ulnar border of the hand to control (e.g., limit) at least one of ulnar abduction, palmar flexion, or dorsal flexion of the hand. In some examples, first lip 15 may extend (e.g., substantially along the X-axis) from a distal end 23 of base 12 to a proximal end 25 of base 12 or any portion thereof. In other examples, first lip 15 includes a plurality of first lips spaced from each other and extending from two or more portions of ulnar side 19 of base 12. The locations of the plurality of first lips may be selected to improve control of at least one of ulnar abduction, palmar flexion, and dorsal flexion of the hand. Control of at least one of ulnar abduction, palmar flexion, and dorsal flexion of the hand using first lip 15 may improve positioning the hand of the patient in the predetermined configuration and/or may help constrain the hand to hold the hand in the predetermined configuration.

In some examples, base 12 defines a second lip 17 instead of or in addition to first lip 15. Second lip 17 (e.g., radial lip) may be configured to engage at least a portion of the radial border of the hand of the patient when the dorsal surface of the hand is engaged with first major surface 20. For example, second lip 17 may extend from base 12 to at least partially surround the radial border of the hand to control (e.g., limit) at least one of radial abduction, palmar flexion, and dorsal flexion of the hand. In some examples, second lip 17 may extend from distal end 23 of base 12 to proximal end 25 of base 12 or any portion thereof. In other examples, second lip 17 includes a plurality of second lips spaced from each other and extending from two or more portions of radial side 21 of base 12. The locations of the plurality of second lips may be selected to improve control of at least one of radial abduction, palmar flexion, and dorsal flexion of the hand. Control of at least one of radial abduction, palmar flexion, and dorsal flexion of the hand using second lip 17 may improve positioning the hand of the patient in the predetermined configuration and/or may help constrain the hand to hold the hand in the predetermined configuration.

By positioning the hand of the patient in a predetermined configuration, base 12 may provide benefits for some medical procedures compared to other compression devices, such as bracelet or band type compression devices, which do not position the hand of the patient in a predetermined configuration. For example, positioning the hand of the patient in a predetermined configuration may improve comfort of the patient by allowing the hand of the patient to be positioned in a natural configuration while the patient is in a supine position. Additionally, or alternatively, positioning the hand of the patient in a predetermined configuration may present the ulnar artery more prominently to reduce the pressure required to achieve compression of the ulnar artery, the ulnar vein, or both.

In some examples, base 12 is formed from one or more substantially rigid materials. A substantially rigid material may include a material having an apparent modulus of rigidity (e.g., apparent shear modulus of elasticity) in ambient conditions sufficient to reduce deflection of base 12 by the hand of the patient before, during, or after a percutaneous coronary procedure. For example, a substantially rigid material may include a material having an apparent shear modulus of at least approximately 0.1 gigapascal (GPa). In some examples, base 12 includes one or more substantially rigid thermoplastics, such as acrylonitrile butadiene styrene (ABS), polyethylene, polycarbonate, polyamide, high impact polystyrene, polypropylene, or polyoxymethylene; or substantially rigid thermoset plastics, such as polyester, polyurethane, or epoxy resin. Base 12 can be entirely rigid in some examples, while in in other examples, base 12 may include one or more flexible regions or joints configured to improve patient comfort when tissue compression device 10 is retained on the hand of the patient.

In the example illustrated in FIGS. 1A and 1B, first major surface 20 is configured to face a dorsal surface of the hand of the patient when tissue compression device 10 is retained on the hand of the patient. In some examples, first major surface 20 may be configured to engage with a dorsal surface of the hand of the patient. For example, base 12 may be configured to support the hand of the patient, position the hand of the patient in the predetermined configuration, limit the movement of one or more portions of the hand or the wrist relative to base 12, or combinations thereof, when the hand is positioned over first major surface 20.

Second major surface 22 faces away from the hand of the patient when the palmar dorsal surface of the hand is facing first major surface 20. In some examples, second major surface 22 is configured to engage with one or more structures to limit mobility the hand of the patient when tissue compression device 10 is retained on the hand of the patient. For example, second major surface 22 may include bands, clips, straps, or the like configured to engage with a portion of an operating table or other device in a surgical suite to limit mobility the hand of the patient when retained in tissue compression device 10. By engaging with one or more structures to limit mobility the hand of the patient, tissue compression device 10 may enable a clinician to position the hand of the patient to present the radial artery and/or the ulnar artery more prominently and improve accuracy of the arteriotomy of the radial artery. In examples in which base 12 is ambidextrous, both first major surface 20 and second major surface 22 may be configured to both face the palmar surface of the hand of the patient or face away from the hand of the patient such that base 12 may be inverted to fit either the left hand or the right hand.

In some examples, base 12 may include a pad disposed on first major surface 20. The pad may be configured to engage with a dorsal surface of the hand of the patient when the hand is positioned over first major surface 20 to improve patient comfort. Additionally, or alternatively, the pad may be configured to position the hand of the patient in a predetermined configuration, as discussed above. For example, the pad may be positioned on base 12 and/or shaped to engage, for example, a portion of the wrist of the patient or the knuckles of the hand to position the hand in the predetermined configuration. In some examples, the pad is formed from a softer, more pliable material than base 12. For example, the pad may include any suitable material, such as silicone, rubber, polyethylene, or a thermoplastic or thermoset plastic, as discussed above.

In some examples, the pad may include an inflatable balloon configured to adjustably control the size and/or rigidity of the pad. Adjustable control of the size and/or rigidity of the pad may enable tissue compression device 10 to accommodate different hand sizes or shapes and adjust the extent to which the pad extends from first major surface 20 to position the hand in the predetermined configuration. The pad may be integrally formed with base 12 or mechanically connected to base 12 by, for example, an adhesive, a hook-and-loop fastener, or any other suitable fastener or combination of fasteners.

In some examples, base 12 includes a coating or other material applied to first major surface 20 (and second major surface 22 in some examples) to increase the static friction between the hand of the patient and base 12, which may reduce any undesirable relative movement between the hand and base 12.

Flexible backing 14, together with base 12, is also configured to help reduce any undesirable relative movement between the hand of the patient and base 12, such as ulnar abduction, radial abduction, palmar flexion, and dorsal flexion of the hand. Control of at least one of ulnar abduction, radial abduction, palmar flexion, and dorsal flexion of the hand using flexible backing 14 may improve positioning the hand of the patient in the predetermined configuration and/or may help constrain the hand during a medical procedure, e.g., without requiring the hand to be taped to a surface on a bed or the like.

Base 12 includes a plurality of base attachment structures 24A and 24B (collectively, "base attachment structures 24"). Base attachment structures 24 are configured to mechanically connect flexible backing 14 to base 12. In some examples, base attachment structures 24 may be defined by first major surface 20. For example, first major surface 20 may define slots 26A and 26B (collectively, "slots 26"). In other examples, base attachment structures 24 may include one or more structures that extend from base 12. In some examples in which base attachment structures 24 extend from base 12, base attachment structures 24 may be continuous with (e.g., integrally formed with) the part of base 12 defining first major surface 20 or physically separate from and mechanically connected to the part of base 12 defining first major surface 20 by, for example, welding, an adhesive, or any other suitable fastener. In an "at rest" state in which no external forces (other than naturally occurring forces) are applied to base attachment structures 24, base attachment structures 24 may extend away from first major surface 20 in any suitable direction, such as parallel to or transverse to first major surface 20.

Although two base attachment structures 24 (in the form of slots 26) are shown in FIGS. 1A and 1B, in other examples, base 12 may include a greater number of base attachment structures (e.g., more than two base attachment structures). Base attachment structures 24 may be configured to mechanically connect flexible backing 14 to base 12. In other examples, base attachment structures 24 may be configured to enable flexible backing 14 to be attached to both first major surface 20 and second major surface 22, such as in examples in which base 12 may be shaped to engage both the left hand of the patient and the right hand of the patient by inverting base 12 to engage the dorsal surface of the hand of the patient with one of the first major surface 20 or second major surface 22.

By mechanically connecting flexible backing 14 to base 12, tissue compression device 10 may better engage the hand of the patient. For example, base attachment structures 24 may enable flexible backing 14 to be tightened on to the hand of the patient prior to or after inflating expandable member 16. Tightening flexible backing 14 to the hand of the patient prior to or after inflating expandable member 16 may maintain a position of expandable member 16 over the ulnar region of the patient while expandable member 16 is inflated. Maintaining the position of expandable member 16 over the ulnar region may more accurately direct pressure to selected tissue near the ulnar artery, the ulnar vein, or both to reduce the amount of pressure to achieve at least partial compression of the ulnar artery, the ulnar vein, or both. Additionally, or alternatively, tightening flexible backing 14 to the hand of the patient prior to or after inflating expandable member 16 may provide pre-compression of selected tissue at the ulnar region to reduce the amount of pressure exerted by expandable member 16 to achieve at least partial compression of the ulnar artery, the ulnar vein, or both.

Flexible backing 14 may be directly or indirectly mechanically connected to base attachment structures 24 using any suitable technique. When connected, base 12 and flexible backing 14 may define a region configured to receive the hand of the patient. For example, the hand of the patient may be inserted or removed from the region defined by (e.g., between) the base 12 and flexible backing 14 when flexible backing 14 is connected to base attachment structures 24, or the hand of the patient may be placed on base 12 before flexible backing 14 is fully connected to base attachment structures 24. In some examples, base attachment structures 24 may be configured to receive flexible backing 14. For example, slots 26 may enable the respective attachment structure of base attachment structures 24 to adjustably mechanically connect flexible backing 14 to base 12. For example, flexible backing 14 may include a hook-and-loop fastener on two portions of flexible backing 14 such that a first portion of the hook-and-loop fastener may extend through an aperture defined by slots 26 to attach to a second portion of the hook-and-loop fastener. In other examples, flexible backing 14 may include a mechanical coupling, such as, for example, a clip, configured to mechanically connect to at least a portion of slots 26.

In some examples, in addition to or instead of base attachment structures 24, another part of base 12 may define one or more base attachment structures configured to receive flexible backing 14 and secure flexible backing relative to base 12. For example, first major surface 20 may define two or more slots defining, for example, a ladder tension lock, a triglide slide, or the like. In other examples, base attachment structures 24 may include any suitable attachment device configured to secure at least a portion of flexible backing 14 to base 12, such as belts, buckle, buttons, or the like.

Flexible backing 14 is configured to engage the hand of a patient when tissue compression device 10 is retained on the hand to urge the hand toward first major surface 20, e.g., to hold the hand of the patient in a predetermined configuration, and to bring expandable member 16 into engagement with selected tissue a the ulnar region of the patient. In the example shown in FIG. 1A, flexible backing 14 defines a first major surface 30 (not visible in FIG. 1A, shown in FIG. 3) and second major surface 32 and includes a plurality of backing attachment structures 34A and 34B (collectively, "backing attachment structures 34").

Flexible backing 14 may include any suitable shape to engage with at least a portion of the hand of the patient. For example, first major surface 30 and second major surface 32 of flexible backing 14 may have a shape corresponds to the anatomical shape of the palmar surface of the hand of a patient to engage with the palmar surface of a hand of a patient. Flexible backing 14 may be shaped to engage with a right hand of the patient, a left hand of the patient, or both the left and the right hand of the patient, e.g., flexible backing 14 may be ambidextrous. In some examples, flexible backing 14 may at least partially conform to a shape of a palmar surface, radial border (FIG. 2), and/or ulnar border (FIG. 2) of the hand of the patient when a dorsal surface of the hand is engaged with first major surface 20 of base 12. By at least partially conforming to the hand of the patient, flexible backing 14 may allow tissue compression device 10 to engage the hand of the patient to position the hand in the predetermined configuration, as discussed above.

In some example, flexible backing 14 includes a substantially inextensible material. A substantially inextensible material may include a material that breaks after being extended between about 10% and about 100% (as measured in accordance with ASTM Standard D638), with a tensile strength between about 20 megapascals (MPa) and about 50 MPa (as measured in accordance with ASTM Standard D412), and/or with an elastic modulus between about 0.1 GPa and about 1 GPa (as measured in accordance with ASTM Standard E2769). For example, when tissue compression device 10 is retained on the hand of the patient, increasing pressure in expandable member 16 (e.g., inflating expandable member 16) results in increasing pressure on tissue at the ulnar region of the patient, rather than resulting in elongation or stretching of flexible backing 14. In this way, flexible backing 14 may conform to a palmar surface of the hand of the patient, and reduce elongation or stretching of flexible backing 14 when expandable member 16 is inflated.

First major surface 30 of backing 14 is configured to face a palmar surface of the hand of the patient when tissue compression device 10 is retained on the hand of the patient such that a dorsal surface of the hand faces base 12. That is, the hand of the patient may be positioned between first major surface 30 of backing 14 and first major surface 20 of base 12. In some examples, first major surface 30 may be configured to engage with a palmar surface of the hand of the patient. For example, flexible backing 14 may be configured to contact the palmar surface and urge the hand of the patient toward base 12 to position the hand of the patient in the predetermined configuration when flexible backing 14 is tightened via base attachment structures 24 and backing attachment structures 34.

Second major surface 32 of flexible backing 14 is configured to face away from the hand of the patient when tissue compression device 10 is retained on the hand of the patient such that a dorsal surface of the hand faces base 12. In examples in which flexible backing 14 is ambidextrous, first major surface 30 and second major surface 32 may be configured to both face the palmar surface of the hand of the patient and face away from the hand of the patient, such that flexible backing 14 may be inverted to fit either the left or right hand.

As illustrated in FIG. 1A, flexible backing 14 includes backing attachment structures 34. Each respective backing attachment structure of backing attachment structures 34 may be configured to adjustably secure flexible backing 14 to a respective attachment structure of base attachment structures 24. For example, backing attachment structure 34A includes a clip configured to mechanically connect flexible backing 14 to base attachment structure 24A that defines slot 26A. Similarly, respective backing attachment structures 34B includes a clip configured to mechanically connect flexible backing 14 to base attachment structures 24B that defines slot 26B. In other examples, respective backing attachment structures 34 may include any suitable corresponding structure configured to mechanically connect to respective base attachment structures 24. In some examples, one or more backing attachment structures of backing attachment structures 34 may enable flexible backing 14 to be tightened on to the hand of the patient prior to or after inflating expandable member 16. In this way, flexible backing 14 may allow tissue compression device 10 to engage the hand of the patient to position the hand of the patient in the predetermined configuration.

In some examples, backing attachment structures 34 and base attachment structures 24 are positioned on flexible backing 14 and base 12, respectively, to provide substantially uniform distribution of force from flexible backing 14 to the hand of the patient when tissue compression device 10 is retained on the hand of the patient. For example, when tissue compression device 10 is retained on the hand of the patient such that the palmar surface faces base 12 and after tightening flexible backing 14 using backing attachment structures 34 and base attachment structures 24, flexible backing 14 may provide a substantially uniform compressive force to at least a portion of the palmar surface of the hand of the patient. Substantially uniform distribution of force from flexible backing 14 to the hand of the patient may improve patient comfort, enable expandable member 16 to provide a substantially uniform compressive force to selected tissue at the ulnar region of the patient, or both.

Expandable member 16 is configured to be positioned over the ulnar region of the patient when tissue compression device 10 is retained on the hand such that the dorsal surface of the hand faces base 12. For example, expandable member 16 may be secured in place to flexible backing 14 at a location that positions expandable member over the ulnar region when tissue compression device 10 is retained on the hand of the patient such that the dorsal surface of the hand faces base 12. In some examples, expandable member 16 may be removably secured to flexible backing 14 such that a clinician may adjust the position of expandable member 16 relative to flexible backing 14 prior to retaining tissue compression device 10 on that hand of the patient. For example, expandable member 16 may be connected to backing 14 via an adhesive, such as a pressure-sensitive adhesive or a removable adhesive, or a mechanical fastener, such as a hook-and-loop mechanism, and a clinician may detach expandable member 16 from backing 14 by pulling expandable member 16 away from backing 14 and then subsequently use the adhesive or hook-and-loop mechanism to reattach expandable member 16 to backing 14 at a different location.

In addition to or instead of the adhesive or a hook-and-loop mechanism, in some examples, backing attachment structures 34 may be configured to adjust the position of expandable member 16 relative to the hand of the patient when tissue compression device 10 is retained on the hand of the patient to position expandable member 16 over the ulnar region. For example, a clinician may adjust one or more backing attachment structures 34 to move the position of expandable member 16 relative to the hand of the patient and position expandable member 16 over the ulnar region.

Expandable member 16 may be mechanically connected to flexible backing 14 by any suitable means, such as, for example, an adhesive, thermal bonding, welding, or a mechanical fastener, e.g., by a hook-and-loop fastener. In other examples, expandable member 16 may be integrally formed with flexible backing 14, such that a position of expandable member 16 is fixed relative to flexible backing 14. For example, flexible backing 14 may include two or more layers forming a pocket and defining expandable member 16.

In some examples, flexible backing 14 and/or expandable member 16 includes a transparent material, such as polypropylene. A transparent flexible backing 14 and/or expandable member 16 may enable a clinician to visualize an access site while tissue compression device 10 is retained on the hand of the patient. In contrast, if flexible backing 14 and/or expandable member 16 was opaque, the clinician would not be able to view the access site. By visualizing the access site, the clinician may visually confirm patent hemostasis.

Expandable member 16 is configured to apply pressure to selected tissue at the ulnar region when tissue compression device 10 is retained on the hand of the patient (such that the dorsal surface faces base 12) to help reduce incidence of radial artery occlusion after percutaneous coronary procedures with transradial access. Expandable member 16 may define any suitable shape having any suitable surface area to apply pressure to selected tissue at the ulnar region. For example, a major surface of expandable member 16 configured to engage with selected tissue at the ulnar region of a patient while the palmar surface of the hand rests on base 12 may define a triangular shape. In other examples, this surface of expandable member 16 may define other geometric shapes, such as an ellipse, a quadrilateral or other polygon, or irregular shapes. Additionally, expandable member 16 define any suitable volume to achieve a selected pressure on the selected tissue at the ulnar region. For example, expandable member 16, when in a deflated configuration or an inflated configuration, may extend any suitable distance from first major surface 30 of flexible backing 14.

Expandable member 16 may include a bladder 36 fluidically connected to a channel 38. Channel 38 may be fluidically connected to one or more inflation devices 37 configured to inflate bladder 36 and one or more deflation devices 39 configured to deflate bladder 36. For example, inflation device 37 may include a pump configured to controllably inflate bladder 36 of expandable member 16 or a syringe configured to controllably inflate bladder 36.

Deflation device 39 may include a release valve configured to deflate bladder 36. In some examples, a clinician may use deflation device 39 to uncontrollably and fully deflate bladder 36, e.g., prior to removing tissue compression device 10 from the hand of the patient. In other examples, deflation device 39 may more controllably deflate bladder 36 to compress of the ulnar region. For example, a clinician may inflate bladder 36 using inflation device 37 to a first pressure that is greater than a minimum pressure to achieve the desired compression of the ulnar region, e.g., the clinician may inflate bladder 36 until the clinician observes at least partial occlusion of the ulnar artery distal to bladder 36 or ulnar vein proximal to bladder 36 by, for example, palpitation, ultrasonography, pulse-oximetry, or modified Allen's test (e.g., the hand of the patient may be elevated, the hand may be clenched in a fist for about 30 seconds, pressure may be applied over the ulnar artery and the radial artery so as to occlude both arteries while the hand is clenched in the fist, the elevated hand may be subsequently unclenched, the color of the hand may be observed as blanched or pallor may be observed at the finger nails, ulnar artery pressure may be released while radial artery pressure is maintained, and the time for color to return to the hand is observed).

After inflating bladder 36 to the first pressure, the clinician may controllably deflate bladder 36 using deflation device 39 to a second pressure slightly less than the minimum pressure to achieve occlusion of the ulnar artery, e.g., the clinician may deflate bladder 36 until the clinician observe return ulnar artery blood flow. After deflating bladder 36 to the second pressure, the clinician may inflate bladder 36 by a predetermined volume, such as, for example, 1 cubic centimeter to 20 cubic centimeters of air, to a third pressure and confirm at least partial occlusion of the ulnar artery. By controllably deflating bladder 36 to the second pressure, the clinician may more accurately inflate bladder 36 to the third pressure using the predetermined volume to sufficiently compress the ulnar region to increase blood flow or blood pressure in the radial artery.

Bladder 36 may define a first major surface facing base 12 and configured to inflate to at least a pressure that provides at least partial occlusion of the ulnar artery. In some examples, inflation of bladder 36 will tend to move the first major surface of bladder 36 away from first major surface 30 of flexible backing 14 and toward first major surface 20 of base 12. When tissue compression device 10 is retained on a hand of the patient, inflation of bladder 36 forces the first major surface of bladder 36 against the tissue at the ulnar artery to provide compression of selected tissue in contact with the first major surface of bladder 36. In this way, expandable member 16 may inflate to apply a selected pressure to tissue at the ulnar region.

Figure 2:
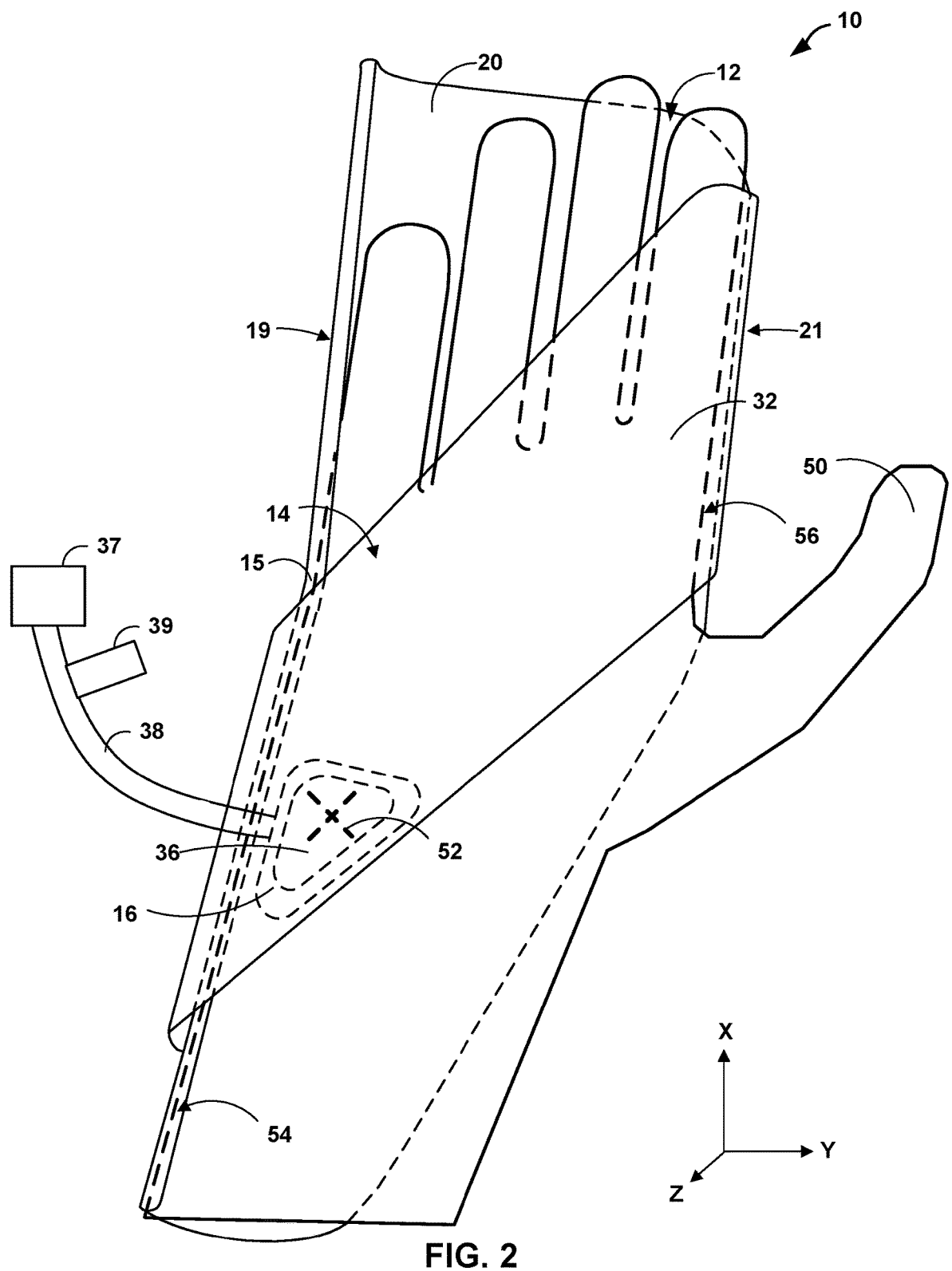
FIG. 2 is a conceptual perspective view illustrating the example tissue compression device of FIG. 1A retained on a hand of a patient.

FIG. 2 is a conceptual perspective view illustrating an example tissue compression device 10 retained on hand 50 of a patient. To improve the clarity of FIG. 2, slots 26, backing attachment structures 34, and second lip 17 are not shown. As discussed above, tissue compression device 10 is configured to engage hand 50 to compress selected tissue 52 at the ulnar region of the patient. Base 12 is shaped to engage hand 50. For example, first major surface 20 of base 12 is shaped and sized to support at least a portion of the wrist of the patient and at least a portion of the dorsal surface of hand 50 including digits of hand 50. In some examples, first major surface 20 of base 12 is shaped and sized to engage at least part of a forearm of the patient, proximal to the wrist. Additionally, as discussed above with respect to FIGS. 1A and 1B, first lip 15 is configured to engage an ulnar border 54 of hand 50 (including a portion of the wrist and/or the forearm) and second lip 17 is configured to engage a radial border 56 of hand 50. In some examples, second lip 17 may engage a radial border of a portion of the wrist and/or the forearm of the patient.

Figure 3A:
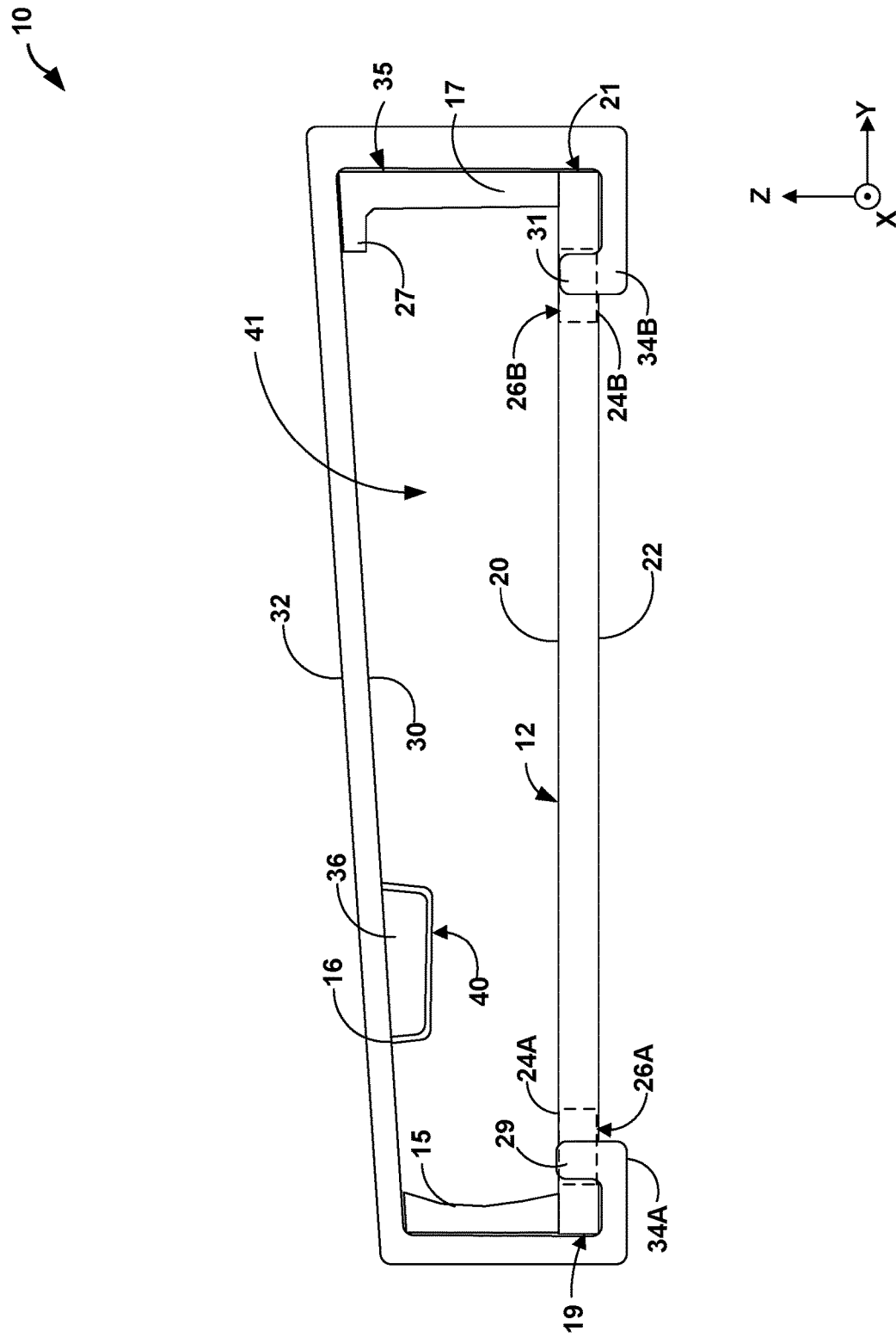
FIGS. 3A and 3B are conceptual side views in the Y-Z and X-Z planes, respectively, illustrating the example tissue compression device of FIG. 1A.
Figure 3B:
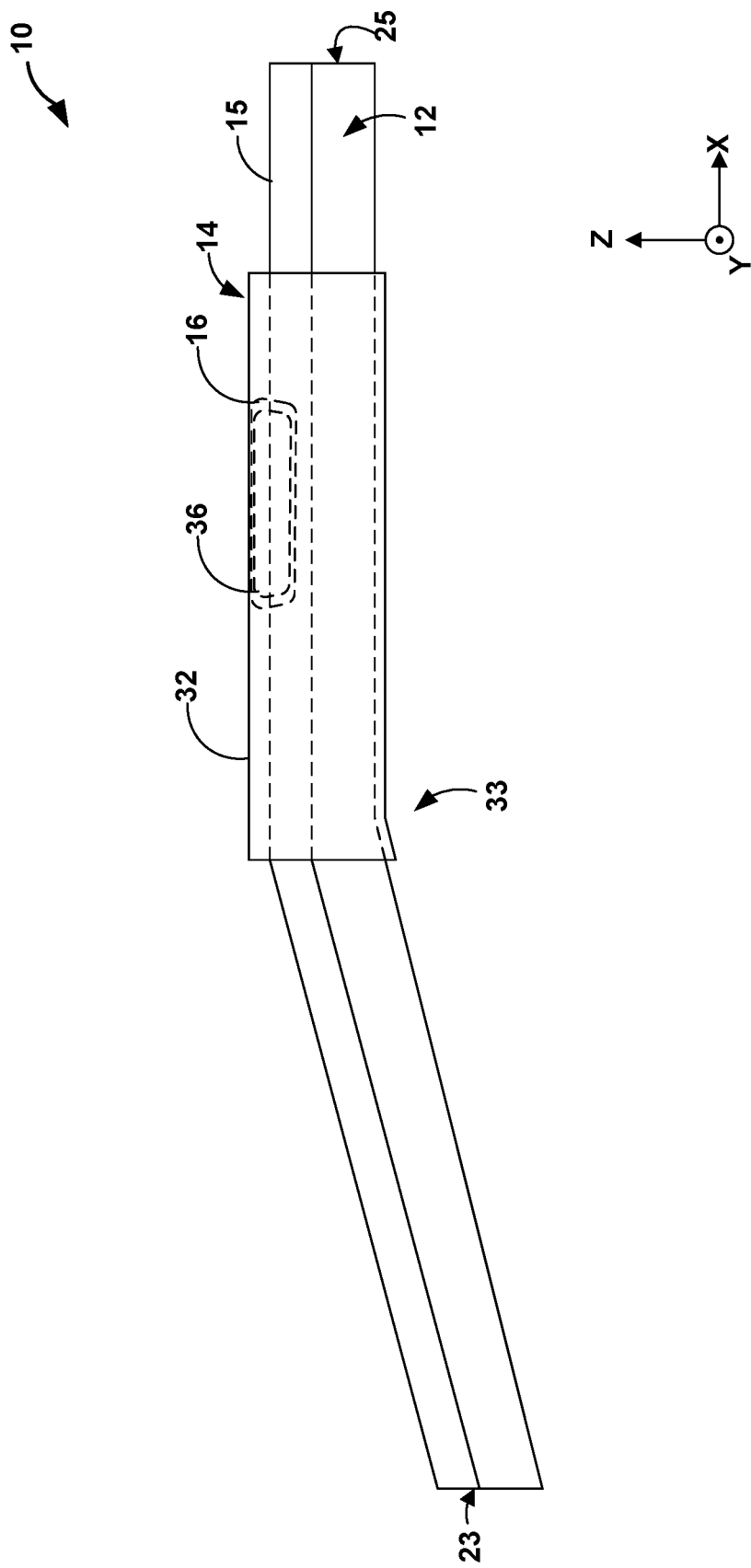

FIGS. 3A and 3B are conceptual side views in the Y-Z and X-Z planes, respectively, illustrating the example tissue compression device 10 of FIG. 1A. As illustrated in FIG. 3A, in some examples, first and second major surfaces 20, 22 of base 12 are substantially flat such that first major surface 20, extending along the Y-axis from radial side 21 to an ulnar side 19, is substantially planar (e.g., planar or nearly planar to the extent permitted by manufacturing and material tolerances). In other examples, first major surface 20 extending along the Y-axis may be curved, for example, to mimic the anatomical contour of the wrist and/or hand of the patient.

As illustrated in FIG. 3B, in some examples, first and second major surfaces 20, 22 of base 12 may include a deflection 33. For example, a proximal portion of base 12 (e.g., extending from proximal end 25 to deflection 33) may extend substantially parallel to the X-axis, while distal portion of base 12 (e.g., extending from deflection 33 to distal end 23) extends at an angle relative to the X-axis. Deflection 33 may include any suitable angle, such as an angle between about 0° and about 90° relative to the X-axis. Deflection 33 may be positioned at the wrist of the patient. By positioning deflection 33 at the wrist, device 10 may be configured to hold a hand of a patient in a predetermined configuration of the hand of the patient in which there is a dorsal flexion (e.g., extension) of the wrist. Dorsal flexion of the wrist may present the radial artery or the ulnar artery more prominently, as discussed above.

As discussed above, base 12 may include first lip 15 and/or second lip 17, which are configured to help hold the hand of the patient in a particular configuration when the dorsal surface of the hand is engaged with first major surface 20 of base 12. In some examples, base 12 may not include one or both of first lip 15 and second lip 17. First lip 15 and second lip 17 may be continuous with (e.g., integrally formed with) base 12 or physically separate from and mechanically connected to the part of base 12 defining first major surface 20 by, for example, welding, an adhesive, or any other suitable fastener. In an "at rest" state in which no external forces (other than naturally occurring forces) are applied to first lip 15 and second lip 17 may extend away from first major surface 20 in any suitable direction. First lip 15 and second lip 17 may include a substantially rigid material, e.g., as discussed above in reference to base 12, or may include a flexible material or one or more flexible regions or joints (e.g., areas of thinner material relative to other portions of the respective lip), which allow the respective lip to deflect, for example, when the hand, the wrist, or the forearm of the patient is received by tissue compression device 10.

In some examples, first lip 15 and second lip 17 may include substantially similar shapes configured to engage both an ulnar side and a radial ride of at least one of the hand, the wrist, or the forearm of the patient. In other examples, first lip 15 and second lip 17 may include dissimilar shapes, such that one of first lip 15 or second lip 17 is configured to engage an ulnar side of at least one of the hand, the wrist, or the forearm of the patient, and the other of first lip 15 and second lip 17 is configured to engage a radial ride of at least one of the hand, the wrist, or the forearm of the patient.

As illustrated in FIG. 3A, first lip 15 may extend from first major surface 20 between about ¼ of an inch (about 0.635 centimeters (cm)) to about 1 inch (about 2.54 cm), such as about ¼ of an inch, in an X-axis direction, which is a direction substantially perpendicular (e.g., perpendicular or nearly perpendicular to the extent permitted by manufacturing tolerances) to first major surface 20. In other examples, first lip 15 may extend any suitable distance from first major surface 20 at any suitable angle relative to first major surface 20 to engage at least a portion of the ulnar border of the hand of the patient when the dorsal surface of the hand is engaged with first major surface 20. First lip 15 may be shaped to mimic the contour of the ulnar side of at least one of the hand, the wrist, or the forearm of the patient. For example, first lip 15 may include a concave surface shaped to receive at least a portion of the ulnar side of at least one of the hand, the wrist, or the forearm of the patient. In other examples, first lip 15 may include other shapes, such as a rectangle.

As illustrated in FIG. 3A, second lip 17 may extend from first major surface 20 between about ¼ of an inch (about 0.635 centimeters (cm)) to about 1 inch (about 2.54 cm), such as about ½ of an inch (about 1.27 cm), in an X-axis direction substantially perpendicular to first major surface 20. In other examples, second lip 17 may extend any suitable distance from first major surface 20 at any suitable angle relative to first major surface 20 to engage at least a portion of the radial border of the hand of the patient when the dorsal surface of the hand is engaged with first major surface 20. Second lip 17 may be shaped to engage the contour of the radial side of at least one of the hand, the wrist, or the forearm of the patient. For example, second lip 17 may include a protrusion 27 extending substantially perpendicular to a planar surface 35 of lip 17. When a dorsal surface of the hand of the patient is positioned over major surface 20, protrusion 27 may extend over at least a portion of the palmar surface of the hand of the patient to, for example, reduce flexion of the wrist of the patient. In other examples, second lip 17 may include other cross-sectional shapes, such as a rectangle, relative to the Y-Z plane.

As discussed above, base attachment structures 24 may be configured to mechanically connect flexible backing 14 to base 12. For example, as shown in FIG. 3A, flexible backing 14 may extend over base 12 to define a region 41 between first major surface 30 of flexible backing and second major surface 20 of base 12 that is configured receive the hand, the wrist, and/or the forearm of the patient. In some examples, flexible backing 14 may extend over first lip 15 and second lip 17 to second major surface 22 of base 12, such as the backing 14 is on both sides of first major surface 20. In other examples, flexible backing 14 may be entirely on one side of first major surface 20. An ulnar side 29 of flexible backing 14 may mechanically couple to slot 26A defined by base 12. Similarly, a radial side 31 of flexible backing 14 may mechanically couple to slot 26B defined by base 12. The mechanical coupling may include any suitable adjustable mechanical coupling, releasable mechanical coupling, fixed mechanical coupling, or combinations thereof including, but not limited to, ladder tension lock, triglide slide, belt, buckle, button, clip, or the like. In examples in which ulnar side 29 or radial side 31 of flexible backing 14 is adjustably mechanically coupled to a respective base attachment structure 24, a position of expandable member 16 relative to the hand, the wrist, or the forearm of the patient may be adjusted to position expandable member 16 over an ulnar region of the patient.

In some examples, bladder 36 of expandable member 16 defines a first major surface 40 facing base 12. Inflation of bladder 36 will tend to move first major surface 40 of bladder 36 away from first major surface 30 of flexible backing 14 and toward first major surface 20 of base 12. When tissue compression device 10 is retained on a hand of the patient such that the dorsal surface of the hand faces first major surface 20 of base 12, inflation of bladder 36 forces first major surface 40 of bladder 36 against the tissue at the ulnar region to provide compression of selected tissue in contact with first major surface 40 of bladder 36. In this way, tissue compression device may compress selected tissue at the ulnar region of the patient to compress the ulnar artery, the ulnar vein, or both. As discussed above, major surface 40 of expandable member 16 may define any suitable shape (e.g., a triangle, pentagon, a circle, an octagon, and the like) configured to engage with the selected tissue region of patient.

Figure 4:
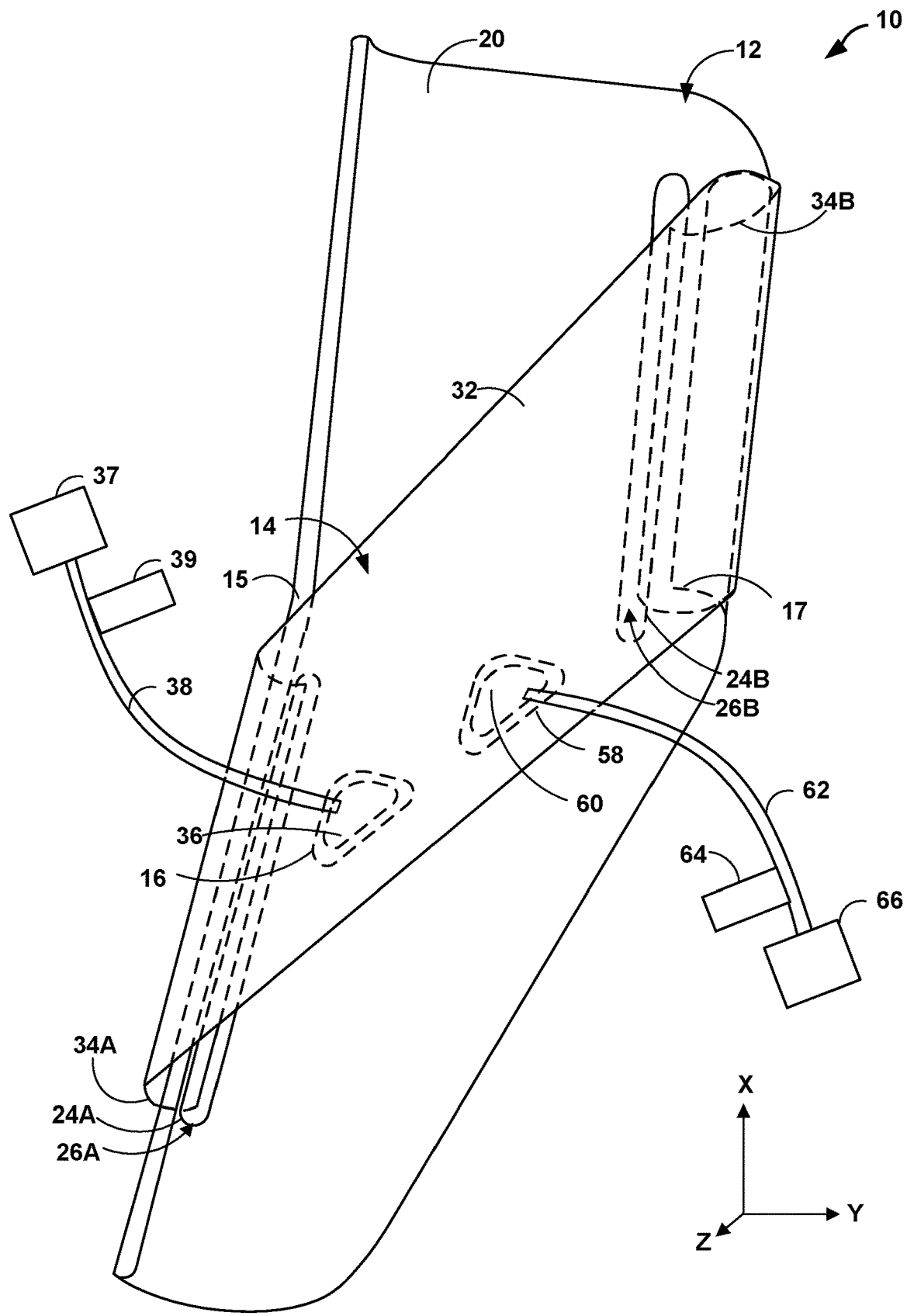
FIG. 4 is a conceptual perspective view illustrating an example tissue compression device including at least two expandable members.

In some examples, tissue compression device 10 is configured to apply pressure to both the ulnar region and a radial region including tissue near a radial artery of the patient. For example, after a transradial percutaneous coronary procedure, a clinician may use tissue compression device 10 to apply pressure to tissue at the radial artery access site to achieve patent hemostasis at the access site. FIG. 4 is a conceptual perspective view illustrating an example tissue compression device 10 including a second expandable member 58 mechanically connected to flexible backing 14. Second expandable member 58 may be substantially similar to expandable member 16, as discussed above, but is configured to be positioned over a radial region of the patient, such as a transradial access site, of the patient when the palmar surface of the hand is engaged with flexible backing 14 and the dorsal surface of the hand is engaged with base 12.

Second expandable member 58 may be positioned on flexible backing 14 relative to expandable member 16 such that second expandable member 58 may be positioned over the radial region when expandable member 16 is positioned over the ulnar region. In some examples, second expandable member 58 may be removably secured to flexible backing 14 such that a clinician may adjust the position of second expandable member 58 relative to flexible backing 14 prior to retaining tissue compression device 10 on that hand of the patient. For example, second expandable member 58 may be connected to backing 14 via an adhesive, such as a pressure-sensitive adhesive or a removable adhesive, or a mechanical fastener, such as a hook-and-loop mechanism. The clinician may detach second expandable member 58 from flexible backing 14 by pulling second expandable member 58 away from flexible backing 14 and then subsequently use the adhesive or hook-and-loop mechanism to reattach second expandable member 58 to flexible backing 14 at a different location.

In addition to or instead of the adhesive or a hook-and-loop mechanism, in some examples, backing attachment structures 34 may be configured to adjust the position of second expandable member 58 relative to the hand of the patient when tissue compression device 10 is retained on the hand of the patient to position second expandable member 58 over the radial region. For example, a clinician may adjust one or more backing attachment structures 34 to move the position of second expandable member 58 relative to the hand of the patient and position second expandable member 58 over the radial region.

Second expandable member 58 may be mechanically connected to flexible backing 14 by any suitable means, such as, for example, an adhesive, thermal bonding, welding, or a mechanical fastener, e.g., by a hook-and-loop fastener. In other examples, second expandable member 58 may be integrally formed with flexible backing 14. For example, flexible backing 14 may include two or more layers forming a pocket and defining second expandable member 58.

In some examples, second expandable member 58 includes a transparent material, such as polypropylene. A transparent second expandable member 58 may enable a clinician to visualize an access site at the radial artery while tissue compression device 10 is retained on the hand of the patient. In contrast, if second expandable member 58 was opaque, the clinician would not be able to view the access site. By visualizing the access site, the clinician may visually confirm patent hemostasis.

Second expandable member 58 is configured to apply pressure to the radial region, e.g., transradial access site, when a dorsal surface of the hand of the patient is engaged with first major surface 20 of base 12. In some examples, positioning the hand of the patient in a predetermined configuration, such as in a dorsal flexion position as discuss above in reference to FIG. 3B, may present the radial artery more prominently to reduce the amount (e.g., duration or pressure) of radial compression required to achieve hemostasis of the radial artery after a percutaneous transradial procedure. Application of pressure to the radial region, e.g., a transradial access site, may be used to cause patent hemostasis of the access site after a percutaneous transradial coronary procedure. Second expandable member 58 define any suitable size and shape having any suitable surface area to apply pressure to selected tissue at the radial region. For example, second expandable member 58 may have a size and shape that are substantially similar to the size and shape of expandable member 16 as discussed above. Additionally, second expandable member 58 define any suitable volume to achieve a selected pressure on the selected tissue at the radial region. For example, second expandable member 58, when in a deflated configuration or an inflated configuration, may extend any suitable distance from first major surface 30 of flexible backing 14.

Similar to expandable member 16, second expandable member 58 includes a bladder 60 fluidically connected to channel 62 that may be connected to one or more inflation devices 66 configured to inflate bladder 60 and one or more deflation devices 64 configured to controllably or uncontrollably deflate bladder 60. In some examples, a clinician may inflate bladder 60 using inflation device 66 to a first pressure that is greater than a minimum pressure to achieve patent hemostasis of a transradial access site, e.g., the clinician may inflate bladder 60 until the clinician visually confirms stoppage of blood flow from the access site. After inflating bladder 60 to the first pressure, the clinician may controllably deflate bladder 60 using deflation device 64 to a second pressure slightly less than the minimum pressure to achieve patent hemostasis, e.g., the clinician may deflate bladder 60 until the clinician visually confirms return blood flow from the access site. After deflating bladder 60 to the second pressure, the clinician may inflate bladder 60 by a predetermined volume, such as, for example, 1 cubic centimeter to 20 cubic centimeters of air, to a third pressure and confirm stoppage of blood flow. In some examples, the third pressure may be sufficient to achieve patent hemostasis of the transradial access site, while preventing occlusion of the radial artery. As discussed above, concurrent compression of the ulnar region also may reduce occlusion of the radial artery by increasing blood flow and/or blood pressure in the radial artery. In this way, the expandable member 16 and the second expandable member 58 may be used together to enable a pressure at the transradial access site via second expandable member 58 sufficient to achieve hemostasis at the transradial access site without causing radial artery occlusion.

Bladder 60 may define a first major surface facing base 12 and is configured to inflate to at least a pressure that provides patent hemostasis of vasculature at the transradial access site. In some examples, inflation of bladder 60 will tend to move the first major surface of bladder 60 away from first major surface 30 of flexible backing 14 and toward first major surface 20 of base 12. When tissue compression device 10 is retained on a hand of the patient, inflation of bladder 60 forces the first major surface of bladder 60 against the tissue at the transradial access site to provide compression of selected tissue in contact with the first major surface of bladder 60.

Figure 5A:
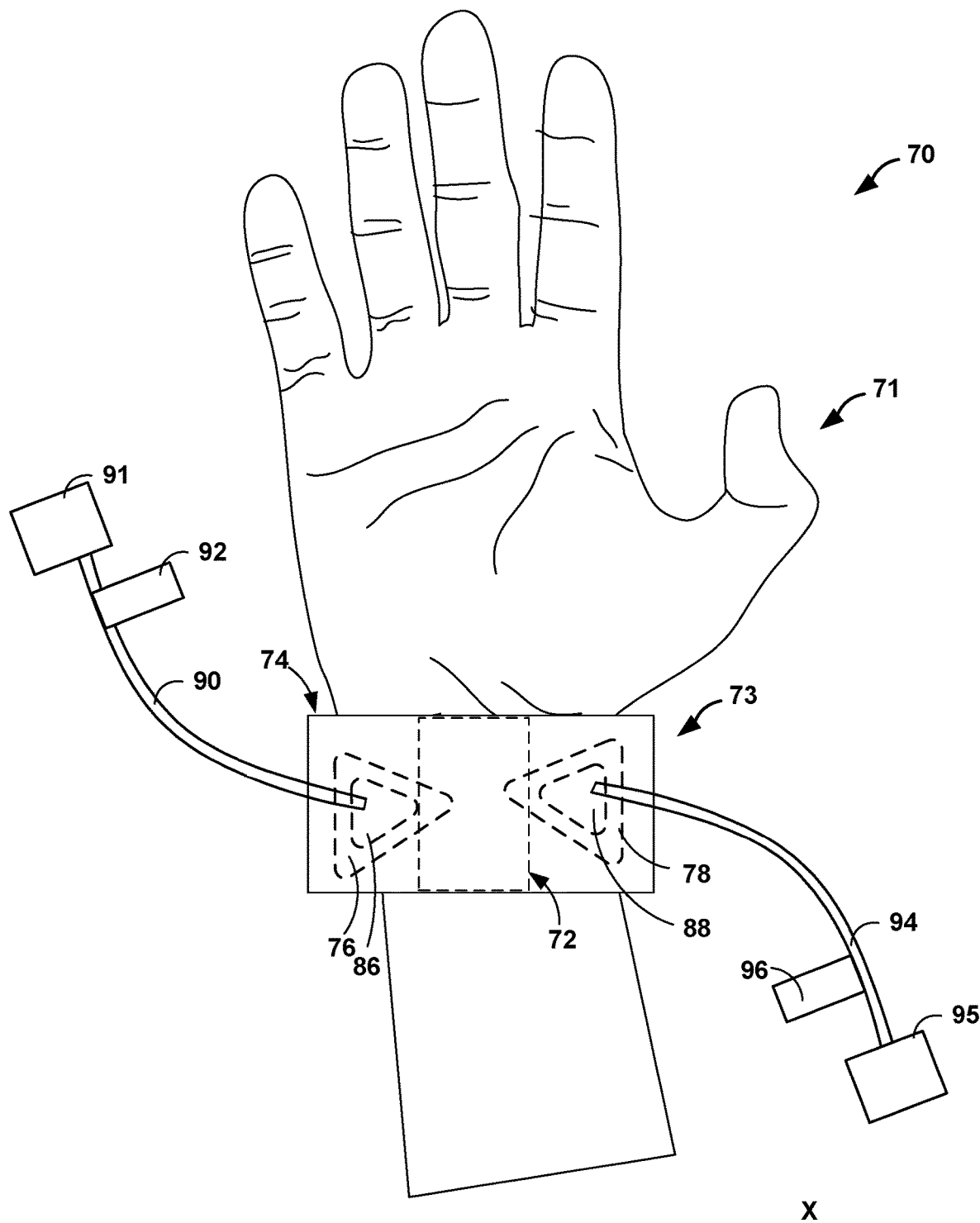
FIGS. 5A and 5B are conceptual plan and side views illustrating an example tissue compression device having a band-type configuration including at least two expandable members.
Figure 5B:
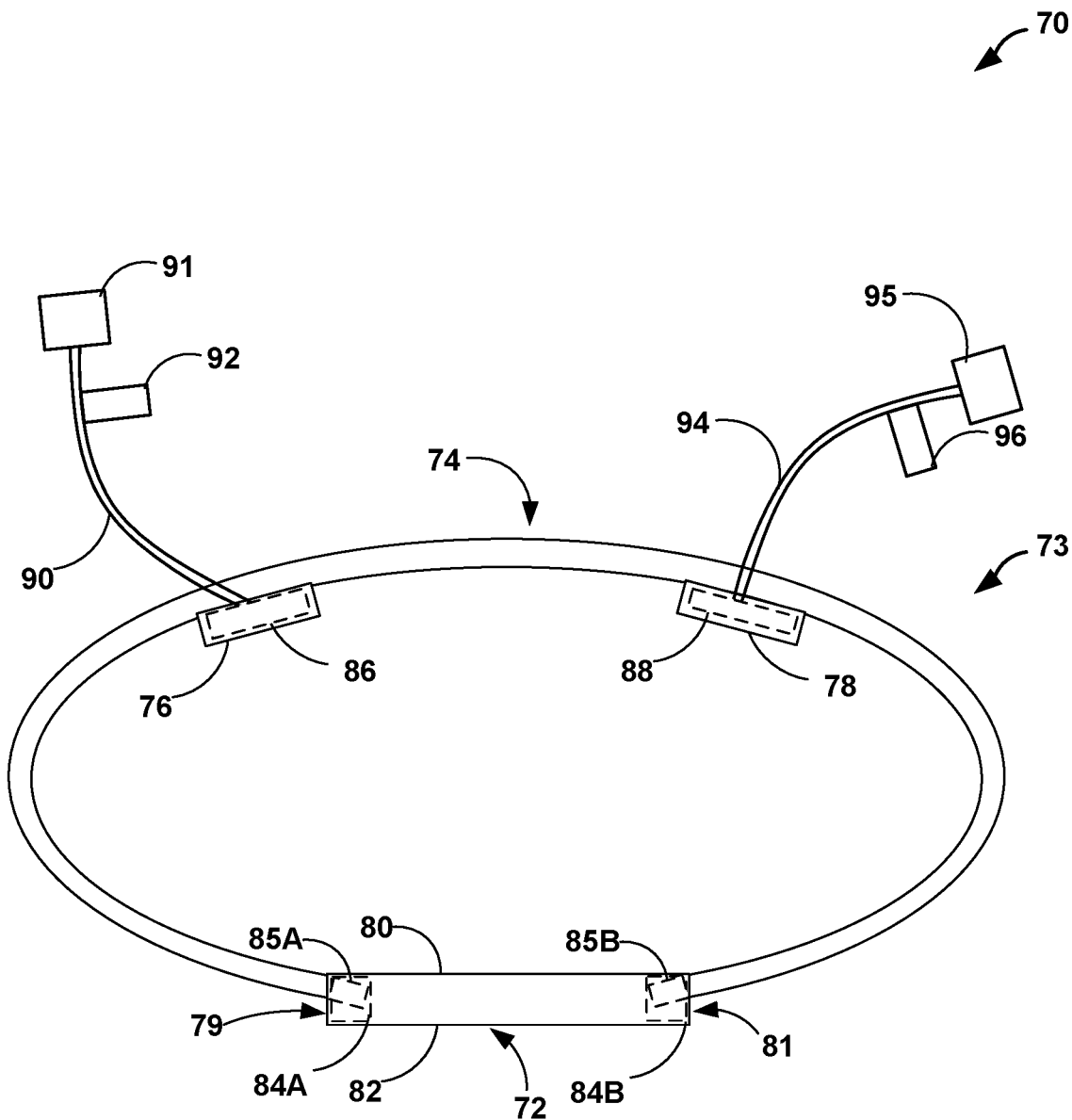

In some examples, a tissue compression device that includes two expandable members may have a band-type (e.g., a bracelet) configuration that is configured to engage less (if any) of a dorsal surface of a hand of a patient than tissue compression device 10. FIGS. 5A and 5B are conceptual plan and side views illustrating an example band-type tissue compression device 70, which includes a band 73, a first expandable member 76 mechanically connected to band 73, a second expandable member 78 mechanically connected to band 73. Tissue compression device 70 is configured to apply pressure to selected tissue at an ulnar region and a radial region of the wrist of arm 71 of the patient to thereby compress tissue near the ulnar artery and/or ulnar vein and the radial artery. Tissue compression device 70 may be configured to simultaneously apply pressure to selected tissue at the ulnar region and the radial region, and, in some examples, a clinician may separately control the pressures applied to the ulnar region and to the radial region via respective and separate expandable members 76 and 78. Tissue compression device 70 may be substantially similar to tissue compression device 10, except for the differences described herein.

Band 73 is configured to engage the wrist of the patient. For example, band 73 may be shaped to surround at least a portion of the wrist of the patient. In some examples, band 73 may be shaped to conform to an anatomical shape of a left wrist of the patient, a right wrist of the patient, or both the left wrist and the right wrist of the patient. Band 73 may be adjustable, such that a tension of band 73 on the wrist of the patient may be adjusted to urge at least one of first expandable member 76 or second expandable member 78 toward the wrist of the patient (e.g., the ulnar region and the radial region, respectively) when the wrist of the patient is engaged with the band. In some examples, band 73 may include base 72 and flexible backing 74. Base 72 and flexible backing 74 may be formed from materials similar to those discussed above with respect to base 12 and flexible backing 14. In other examples, however, base 12 and flexible backing 14 may be formed from the same material or materials having substantially similar properties (e.g., similar hardnesses). In some examples, base 72 and flexible backing 74 may be physically separate components mechanically connected to form band 73. In some examples, base 72 and flexible backing 74 may be integrally formed.

Base 72 defines a first major surface 80 and a second major surface 82 on an opposite side of base 72 from first major surface 80, and includes at least one base attachment structure 84A and 84B ("base attachment structures 84"). Although two base attachment structures 84 are shown in FIGS. 5A and 5B, in other examples, base 72 may only include one base attachment structure with which flexible backing 74 may attach to base 72. In addition, as discussed above, in some examples, base 72 and flexible backing 74 may be integrally formed, in which case base 72 would not define any base attachment structures.

Base 72 may be substantially similar to base 12 described in reference to FIGS. 1A and 1B, except for the differences described herein. Base 72 is configured to engage a left wrist of the patient, a right wrist of the patient, or both the left wrist and the right wrist of the patient. For example, base 72 may extend any suitable distance around a wrist of the patient. First major surface 80 may include any suitable shape (in the Y-Z plane shown in FIG. 5B) configured to engage with at least a portion of the wrist of the patient, such as elliptical, rectangular, or irregular shapes. In some examples, base 72 may have a shape in the Y-Z plane that corresponds to an anatomical shape of at least part of a wrist of the patient (e.g., mimics the general contour of the wrist or part of the wrist). Second major surface 82 may be shaped the same as or substantially similar to first major surface 80, such that a thickness of base is substantially uniform from an ulnar side 79 of base 72 to a radial side 81 of base 72. In other examples, second major surface 82 may be substantially planar to enable base 72 to engage with a flat surface, such as an operating table.

Base attachment structures 84 may be substantially similar to base attachment structures 24 described in reference to FIG. 1A, except for the differences described herein. For example, base attachment structures 84 configured to adjustably mechanically connect flexible backing 74 to base 72 to enable flexible backing 74 to be tightened on to the wrist of the patient prior to or after inflating first and second expandable members 76 and 78. Tightening flexible backing 74 on to the wrist of the patient may maintain a position of first and second expandable members 76 and 78 over the ulnar region and the radial region of the patient, provide pre-compression of selected tissue at the ulnar region, the radial region, or both. Maintaining a position of first and second expandable members 76 and 78 over the ulnar region and the radial region of the patient may more accurately direct pressure to achieve compression of the ulnar region and the radial region. Providing pre-compression of selected tissue at the ulnar region and/or the radial region may reduce the amount of pressure exerted by first expandable member 76 to achieve compression of the ulnar artery, ulnar vein, or both, as well as the pressure exerted by second expandable member 78 to achieve patent hemostasis of a transradial access site at the radial region.

Flexible backing 74 may be substantially similar to flexible backing 14 described in reference to FIG. 1A, except for the differences described herein. Flexible backing 74 is configured to engage a left wrist of the patient, a right wrist of the patient, or both the left wrist and the right wrist of the patient. For example, flexible backing 74 may define a band having a width (measured along the X-axis) of between about 1 inch (2.54 cm) to about 4 inches (10.16 cm) and a length (measured circumferentially in the Y-Z plane) sufficient to surround the wrist, such as between about 4 inches (10.16 cm) to about 12 inches (25.4 cm). The cross-sectional shape of flexible backing 14 in the Y-Z plane may include any suitable shape, such as rectangular, elliptical, other geometry shapes, or irregular shapes. The shape of flexible backing may be selected to improve patient comfort, reduce movement of flexible backing when tissue compression device 70 is retaining on the wrist of the patient, or both.

In examples in which flexible backing 74 is separate from and connected to base 72, flexible backing 74 may include at least one (e.g., one or more) backing attachment structure 85A and 85B ("backing attachment structures 85"). Backing attachment structures 85 may be substantially similar to backing attachment structures 34 described in reference to FIG. 1A, except for the differences described herein. For example, backing attachment structures 85 may be configured to adjustably secure flexible backing 74 to a respective attachment structure of base attachment structures 84.

First and second expandable members 76 and 78 may be the substantially similar to expandable member 16 describe in reference to FIG. 1A, except for the differences described herein. For example, first expandable member 76 and second expandable member 78 may be fixed to or adjustably positioned on band 73 relative to each other to enable first expandable member 76 to be positioned over the ulnar region of the patient and to enable second expandable member 78 to be positioned over the radial region of the patient when tissue compression device 70 is retained on the wrist of the patient. In some examples, first expandable member 76 may be mechanically connected to at least one of base 72 or flexible backing 74. In some examples, second expandable member 78 may be mechanically connected to at least one of base 72 or flexible backing 74. In some examples, first expandable member 76 may include a first bladder 86 fluidically connected to inflation device 91 and deflation device 92 by channel 90. In some examples, second expandable member 78 may include a second bladder 88 fluidically connected to inflation device 95 and deflation device 96 by channel 94.

In other examples, first expandable member 76 and second expandable member 78 may be fluidically connected to a common channel including one or more valves to fluidically isolate first expandable member 76 and/or second expandable member 78 from one or more inflation devices and one or more deflation devices. Inflation devices 91 and 95 may be substantially the same as inflation devices 37, and deflation devices 92 and 96 may be substantially the same as deflation devices 39, described in reference to FIG. 1A. In some examples, first bladder 86 may be configured to inflate to at least a pressure to cause compression of tissue near an ulnar artery of the patient. For example, inflation (or a series of inflations and deflations) of first bladder 86 may be used to compress the ulnar region of the patient to increase blood flow or blood pressure in the radial artery of the patient. In some examples, second bladder 88 may be configured to inflate to at least a pressure to cause patent hemostasis of a vascular access site at the radial artery of the patient. For example, inflation (or a series of inflations and deflations) of second bladder 88 may be used to compress the radial region of the patient to achieve patent hemostasis of a transradial access site at a radial artery of the patient.

Figure 6:
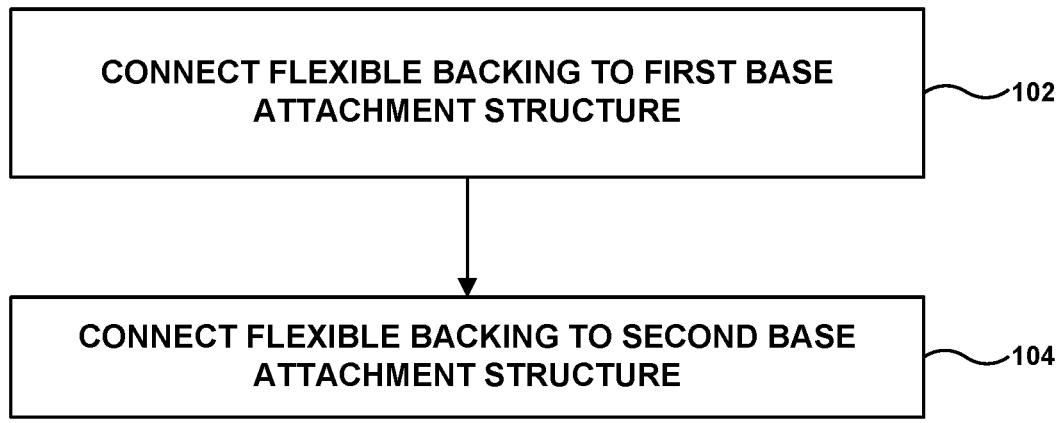
FIG. 6 is a flow diagram illustrating an example method of assembling a tissue compression device including a flexible backing adjustably mechanically connected to a base and an expandable member mechanically connected to the flexible backing.

The tissue compression devices described herein may be assembled using any suitable technique. FIG. 6 is a flow diagram illustrating an example method of assembling an example tissue compression device including a base, a flexible backing adjustably mechanically connected to the base, and an expandable member mechanically connected to the flexible backing. The tissue compression device may be the same as or substantially similar to tissue compression device 10 discussed above with respect to FIGS. 1A-5B. Although FIG. 6 is described with respect to tissue compression device 10, in other examples, the method of FIG. 6 may be used to assemble or use other tissue compression devices, such as tissue compression device 70, or tissue compression devices including a flexible backing adjustably mechanically connected to a base and an expandable member mechanically connected to the flexible backing.

In accordance with the method shown in FIG. 6, a user or a device mechanically connects flexible backing 14 of tissue compression device 10 to first base attachment structure 24A of a plurality of base attachment structures 24 defined by or extending from first major surface 20 of base 12 of tissue compression device 10 (102). For example, mechanically connecting flexible backing 14 to base 12 may include securing backing attachment structure 34A to slot 26A with a clip or other mechanical fastener. The method also includes mechanically connecting flexible backing 14 to second base attachment structure 24B of the plurality of base attachment structures 24 (104), such as by securing backing attachment structure 34B to slot 26B with a clip or other mechanical fastener. Flexible backing 14 may be mechanically connected to base 12 using the technique shown in FIG. 6 before or after the dorsal surface of the hand of the patient is positioned on first major surface 20.

In some examples, after flexible backing 14 is connected to base 12 and while the dorsal surface of the hand of the patient is engaged with first major surface 20 of base 12, the user may tighten flexible backing 14 onto the palmar surface of the hand of the patient in order to bring expandable member 16 into better engagement with selected tissue of the patient. For example, the user may pull backing attachment structures 34A and 34B further through the respective slots 26A and 26B.

In some examples, the method of FIG. 6 may be part of a method of forming or assembling tissue compression device 10 and may further include, before mechanically connecting flexible backing 14 to base 12, thermoforming or molding base 12. Base 12 may include a substantially rigid thermoplastic configured to be thermoformed to substantially conform to an anatomical shape of at least one of the hand, the wrist, or the forearm of the patient or a substantially rigid thermoset plastic configured to be molded to substantially conform to an anatomical shape of at least one of the hand, the wrist, or the forearm of the patient. By thermoforming or molding base 12 to conform to an anatomical shape of at least one of the hand, the wrist, or the forearm of the patient, base 12 may be shaped to improve patient comfort, present the ulnar artery or radial artery more prominently, or both.

In some examples, base 12 is configured to position the hand of the patient in a predetermined configuration when the dorsal surface of the hand is engaged with first major surface 20 of base 12 using a selected shape of at least one of first major surface 20, first lip 15, or second lip 17. In examples in which base 12 includes a pad disposed on base 12, assembling tissue compression device 10 may include positioning the pad on base 12 such that the pad is configured to engage at least a portion of the dorsal surface of at least one of the hand, the wrist, or the forearm of the patient to position at least one of the hand, the wrist, or the forearm of the patient of the patient in the predetermined configuration when the dorsal surface of the hand is engaged with first major surface 20 of base 12. In examples in which base 12 includes first lip 15 and/or second lip 17, assembling tissue compression device 10 may include integrally forming first lip 15 and/or second lip 17 with base 12, or forming first lip 15 and/or second lip 17 that is physically separate from base 12 and attaching first lip 15 and/or second lip 17 to base 12, such that first lip 15 and/or second lip 17 is configured to control at least one of radial abduction, ulnar abduction, palmar flexion, or dorsal flexion of the hand the patient when the dorsal surface of the hand is engaged with first major surface 20 of base 12 to help keep the hand in the predetermined configuration.

As discussed above, base 12 may include at least one base attachment structure 24 that is integrally formed with the first major surface 20. In other examples, assembling tissue compression device 10 may include attaching at least one base attachment structure of the plurality of base attachment structures 24 that is physically separate from first major surface 20 to first major surface 20. In some examples, at least one attachment structure of the plurality of base attachment structures extend away from the major surface in a direction parallel to and/or transverse to the major surface.

Figure 7:
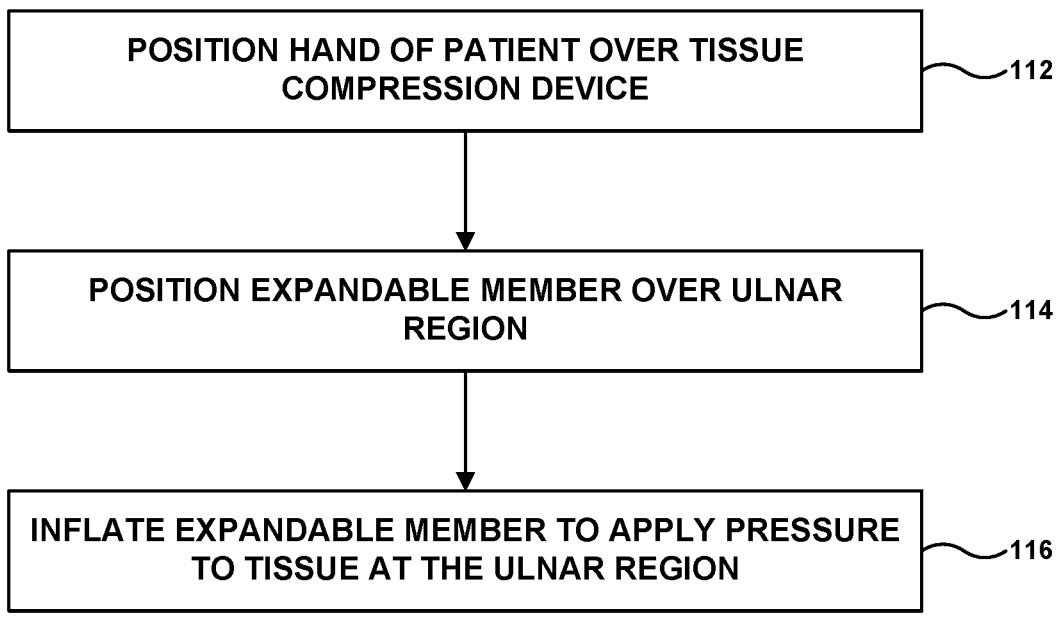
FIG. 7 is a flow diagram illustrating an example method of using a tissue compression device including a flexible backing adjustably mechanically connected to a base and an expandable member mechanically connected to the flexible backing.

The tissue compression devices describe herein may be retained on a hand of a patient using any suitable technique. FIG. 7 is a flow diagram illustrating an example method of using a tissue compression device including a base, a flexible backing adjustably mechanically connected to the base, and an expandable member mechanically connected to the flexible backing to a patient. The tissue compression device may be the same as or substantially similar to tissue compression device 10 discussed above with respect to FIGS. 1A-5B. Although FIG. 7 is described with respect to tissue compression device 10, in other examples, the method of FIG. 7 may be used with other tissue compression devices, such as tissue compression device 70, or tissue compression devices including a flexible backing adjustably mechanically connected to a base and an expandable member mechanically connected to the flexible backing.

The method shown in FIG. 7 includes positioning a dorsal surface of a hand of a patient over base 12 of tissue compression device 10 (112). In some examples, the hand of the patient may be positioned over first major surface 20 of base 12 while base 12 and flexible backing 14 are mechanically connected to each other, such as by sliding the hand between the region defined between base 12 and flexible backing 14 when flexible backing 14 is connected to base 12. In other examples, the hand of the patient may be positioned on first major surface 20 of base 12 while flexible backing 14 is mechanically separated from base 12, and, after the hand is positioned on first major surface 20, flexible backing 14 may be mechanically connected to base 12.

The method of FIG. 7 also includes positioning expandable member 16 over an ulnar region of the patient (114). In some examples, expandable member 16 is mechanically connected to flexible backing 14, such that positioning expandable member 16 over the ulnar region may include tightening flexible backing 14 over the palmar surface of the hand of the patient while the dorsal surface is engaged with first major surface 20 of base 12. Depending on the anatomy of the patient, a user may also adjust the position of expandable member 16 relative to the hand of the patient, such as by repositioning flexible backing 14 relative to base 12 using the base attachment structure 24 and the backing attachment structures 34 (e.g., tightening and loosening as needed to move expandable member 16 relative to base 12). In some examples, expandable member 16 is movable relative to backing 14, and a user may detach expandable member 16 from backing 14 and then subsequently reattaching expandable member 16 to backing 14 at a different location, thereby enabling a user to adjust the position of expandable member 16 relative to base 12 and the hand of the patient.

The method of FIG. 6 also includes inflating expandable member 16 to apply pressure to tissue at the ulnar region (116). For example, expandable member 16 includes bladder 36 such that inflating expandable member 16 includes inflating bladder 36 to cause compression of tissue near the ulnar artery. In some examples, base 12 includes a substantially rigid thermoplastic or a substantially rigid thermoset plastic, and flexible backing 14 includes a substantially inextensible material, such that when tissue compression device 10 is retained on the hand of the patient, the hand is constrained between the substantially rigid base 12 and flexible backing 14 and increasing pressure in expandable member 16 results in increasing pressure on selected tissue at the ulnar region of the patient, rather than resulting in elongation or stretching of flexible backing 14.

In examples in which tissue compression device 10 includes second expandable member 58 mechanically connected to flexible backing 14, the technique may include, after positioning the dorsal surface of the hand of the patient on first major surface 20 of base 12, adjusting a position of second expandable member 58 to position second expandable member 58 over a radial artery of the patient, such as, for example, over a transradial access site. The technique also may include, after adjusting a position of second expandable member 58, inflating second expandable member 58 to apply pressure to a radial artery of the patient to cause patent hemostasis of a vascular access site at the radial artery. In some examples, the technique may also include, after positioning the dorsal surface of the hand of the patient on first major surface 20 of base 20, inflating second expandable member 58 to apply pressure to a radial artery of the patient, e.g., to attempt to achieve or to actually achieve patent hemostasis of a vascular access site at the radial artery.

Various examples have been described. Any combination of the described systems, devices, operations, or functions is contemplated. These and other examples are within the scope of the following claims.

What is claimed is:

1. A tissue compression device comprising:
   a band configured to engage a wrist of a patient, the band comprising:
      a base comprising at least one base attachment structure and a major surface configured to engage a first portion of the wrist of the patient; and
      a flexible backing comprising at least one backing attachment structure and configured to engage a second portion of the wrist of the patient,
      wherein the at least one backing attachment structure is configured to adjustably mechanically connect the flexible backing to the at least one base attachment structure;
   a first expandable member directly mechanically connected to the flexible backing, wherein the first expandable member is configured to be positioned over an ulnar region of the patient when the band is engaged with the wrist of the patient, the first expandable member being configured to apply pressure to the ulnar region; and
   a second expandable member directly mechanically connected to the flexible backing, wherein the second expandable member is configured to be positioned over a radial region of the patient when the band is engaged with the wrist of the patient, the second expandable member being configured to apply pressure to the radial region, and wherein the first expandable member and the second expandable member are connected to the same flexible backing.

2. The tissue compression device of claim 1, wherein the first expandable member comprises a first bladder configured to inflate to at least a pressure to cause compression of tissue near an ulnar artery of the patient, and wherein the second expandable member comprises a second bladder configured to inflate to at least a pressure to cause patent hemostasis of a vascular access site at a radial artery of the patient.

3. The tissue compression device of claim 1, wherein at least one of the first expandable member or the second expandable member is removably mechanically connected to the band.

4. The tissue compression device of claim 1, wherein at least one of the first expandable member or the second expandable member is integrally formed with the band.

5. The tissue compression device of claim 1, wherein the at least one backing attachment structure is configured to adjust a tension of the flexible backing to urge at least one of the first expandable member or the second expandable member toward the wrist of the patient when the wrist of the patient is engaged with the band.

6. The tissue compression device of claim 1, wherein the base comprises a substantially rigid thermoplastic or a substantially rigid material and the flexible backing comprises a substantially inextensible material.

7. The tissue compression device of claim 1, wherein the first portion of the wrist is different from the second portion of the wrist, and wherein the first portion and the second portion define an outer perimeter of the wrist.

8. The tissue compression device of claim 1, wherein the base extends circumferentially from a first end to a second end, and wherein the flexible backing extends circumferentially from the first end of the base to the second end of the base.

9. The tissue compression device of claim 1, wherein the at least one backing attachment structure is disposed at one end of the flexible backing and is separate from the first expandable member and the second expandable member along the length of the flexible backing.

\* \* \* \* \*